(12) United States Patent
Xia

(10) Patent No.: US 11,878,065 B2
(45) Date of Patent: Jan. 23, 2024

(54) REPORTER PROTEIN FUSED ANTIBODIES

(71) Applicant: Xiaofeng Xia, Wynnewood, PA (US)

(72) Inventor: Xiaofeng Xia, Wynnewood, PA (US)

(*) Notice: Subject to any disclaimer, the term of this patent is extended or adjusted under 35 U.S.C. 154(b) by 127 days.

(21) Appl. No.: 16/535,203

(22) Filed: Aug. 8, 2019

(65) Prior Publication Data

US 2020/0046857 A1  Feb. 13, 2020

Related U.S. Application Data

(60) Provisional application No. 62/715,971, filed on Aug. 8, 2018.

(51) Int. Cl.

| | |
|---|---|
| *A61K 49/00* | (2006.01) |
| *G01N 33/566* | (2006.01) |
| *G01N 33/542* | (2006.01) |
| *G01N 33/68* | (2006.01) |
| *C07K 16/18* | (2006.01) |
| *G01N 33/563* | (2006.01) |

(52) U.S. Cl.
CPC .......... *A61K 49/0058* (2013.01); *C07K 16/18* (2013.01); *G01N 33/542* (2013.01); *G01N 33/563* (2013.01); *G01N 33/566* (2013.01); *G01N 33/6845* (2013.01); *C07K 2319/02* (2013.01); *C07K 2319/06* (2013.01); *C07K 2319/60* (2013.01); *C07K 2319/70* (2013.01)

(58) Field of Classification Search
CPC ............... G01N 33/566; G01N 33/563; C07K 2319/70; C07K 2319/02; C07K 2319/61; C07K 2319/60
See application file for complete search history.

(56) References Cited

U.S. PATENT DOCUMENTS

| | | | |
|---|---|---|---|
| 7,750,204 B2 * | 7/2010 | Kodama | C07K 14/005 800/18 |
| 2004/0117863 A1 * | 6/2004 | Edge | C07K 16/04 800/7 |
| 2010/0267145 A1 * | 10/2010 | Mihara | C12N 5/0636 435/456 |
| 2011/0200601 A1 * | 8/2011 | Stanley | C07K 16/18 424/135.1 |
| 2015/0191710 A1 * | 7/2015 | Lee | C07K 16/1072 435/188 |

FOREIGN PATENT DOCUMENTS

CN   105646704 A  *  6/2016  ......... A01K 67/0278

OTHER PUBLICATIONS

Sato (Nature Biotechnology 2002 vol. 20, p. 287-294). (Year: 2002).*
Grant (Biphysical Journal: Biophysical Letters 2008 pp. L69-L71). (Year: 2008).*
Wegner (ACS Nano 2013 vol. 7:7411-7419). (Year: 2013).*
CN105646704 English Translation publication date Jun. 8, 2016 (Year: 2016).*
Shen (Chem Rev 2014 114:7631-7677). (Year: 2014).*

* cited by examiner

*Primary Examiner* — Changhwa J Cheu
(74) *Attorney, Agent, or Firm* — Riverside Law LLP

(57) ABSTRACT

The present invention relates to reporter protein fusion antibodies, transgenic animals expressing the same, and methods of using the reporter protein fusion antibodies.

2 Claims, 16 Drawing Sheets

Specification includes a Sequence Listing.

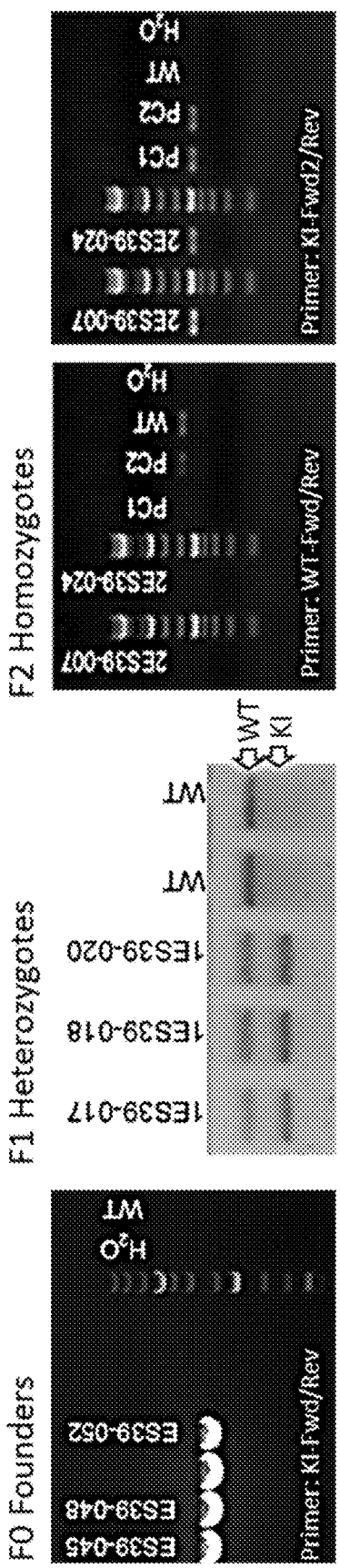
Fig. 5A
Fig. 5B

REPORTER PROTEIN FUSED ANTIBODIES

CROSS REFERENCE TO RELATED APPLICATIONS

This application claims priority to U.S. Provisional Application No. 62/715,971, filed Aug. 8, 2018 which is hereby incorporated by reference herein in its entirety.

BACKGROUND OF THE INVENTION

An antibody recognizes an antigen through a paratope it contains that specifically interacts with a particular epitope on the antigen it binds. Such specific antibody-antigen interactions have wide applications, including applications in antigen detection and clinical diagnosis.

In order to detect the antibody-antigen interaction the antibody or antigen is often tagged with a signal generating molecule. These molecules include small chemicals capable of producing light, electric, sonic, or magnetic signals, and reporter proteins that can similarly produce the above detectable signals, mostly light signals that are colorimetric, fluorescent, or bioluminescent. The signal generating chemicals or reporter proteins are usually conjugated to the antibodies or antigens through chemical reactions to certain type of amino acids at specified or unspecified sites. Such conjugated products are undefined and the composition is heterogenous. The conjugation site on the antibody or antigen may also affect the antibody-antigen interaction and impact the immunoassay.

Molecular biology techniques allow for the fusion of a reporter protein to an antibody. The resulting reporter protein fused antibody represents a number of advantages over the chemically conjugated antibodies, including (1) it is a fully defined molecule, in contrast to the heterogenous chemically conjugated antibodies; (2) it has a strict reporter/antibody stoichiometry, again in contrast to the heterogenous chemically conjugated antibodies; (3) it allows bypassing the need of labeled secondary antibodies to simplify the immunoassay procedure. However, methods for producing and using reporter protein fusion antibodies are still lacking.

An immunoassay is a biochemical test to measure the presence or concentration of an analyte molecule through the use of an antibody or antigen. Immunoassays come in many different formats and variations. It may be run as a heterogeneous immunoassay in multiple steps during which the bound and unbound antibodies are separated at different points. It may also be carried out as a homogenous immunoassay without the need of a separation step. Due to the simpler procedure, homogenous immunoassays represent a significant advantage in assay automation, miniaturization, as well as multiplexing.

Proximity assays utilize physics mechanisms to generate signals when two or more molecules are brought to close proximity. Proximity assays are homogeneous assays that do not require a separation step. Proximity assays are widely used in studying protein-protein interactions and are less common in immunoassays. Proximity assays using reporter protein fused antibodies have not been reported.

Transgenic animals are animals with a foreign gene deliberately inserted into their genome. A transgenic animal can be created by the microinjection of foreign DNA into the pronuclei of a fertilized egg that is subsequently implanted into the oviduct of a pseudopregnant surrogate mother. A transgenic animal can also be created using embryonic stem cells that are transfected with the foreign DNA by microinjecting the transfected embryonic stem cells into an embryo at the blastocyst stage of development and subsequently implanting the embryo into the oviduct of a pseudopregnant surrogate mother. The protein coded by the foreign gene will be produced in the transgenic animal, either alone as a separate protein or fused to an endogenous protein depending on the design.

When a reporter protein coding DNA is selectively inserted to one end of an immunoglobulin gene, the transgenic animal will produce reporter protein fused antibodies. Such antibodies are fully defined homogenous molecules. When the reporter gene is fused to one end of an immunoglobulin constant region gene, the transgenic animal is predicted to produce a highly diverse library of antigen specific reporter protein fused antibodies upon immunization. The transgenic animal's antibody repertoire provides an ideal source for screening reporter protein fused antibodies that may be used in immunoassays. To date such a transgenic animal has not been generated.

Thus, there is a need in the art for novel methods employing reporter protein fused antibodies and for transgenic animals expressing reporter protein fused antibodies. The present invention satisfies this unmet need.

SUMMARY OF THE INVENTION

In one embodiment, the invention relates to a composition comprising a reporter protein fusion antibody comprising an antigen-binding domain linked to a reporter protein, or fragment thereof.

In one embodiment, the reporter protein is a fluorescent protein including, but not limited to, green fluorescence protein (GFP) and variants thereof, a resonance energy transfer (RET) donor molecule, a RET acceptor molecule, a protein-fragment complementation assay (PCA) bait protein, a PCA prey protein, horseradish peroxidase (HRP), alkaline phosphatase (AP), a luciferase including, but not limited to, firefly luciferase, Renilla luciferase, deep sea shrimp luciferase and variants thereof, β-galactosidase, chloramphenicol acetyl transferase, glucose oxidase, acetate kinase, xanthine oxidase, or glucose 6-phosphate dehydrogenase.

In one embodiment, the invention relates to a nucleic acid molecule encoding a reporter protein fusion antibody comprising an antigen-binding domain linked to a reporter protein, or fragment thereof.

In one embodiment, the invention relates to a transgenic animal, comprising a nucleic acid molecule encoding a reporter protein fusion antibody comprising an antigen-binding domain linked to a reporter protein, or fragment thereof.

In one embodiment, the animal is a mouse, a rat, a dog, a rabbit, a pig, a guinea pig, a donkey, a sheep, a goat, a chicken, a cow, a llama or a camel.

In one embodiment, the invention relates to a method of selecting a reporter protein fusion antibody for use in a method of detecting one or more target molecules in a sample. In one embodiment, the invention relates to a method of selecting a reporter protein fusion antibody for use in a method of detecting at least two target molecules in close proximity in a sample. In one embodiment, the method comprises a) isolating one or more reporter protein fusion antibody, wherein the reporter protein fusion antibody comprises an antigen-binding domain linked to a reporter protein or fragment thereof selected from the group consisting of a RET donor molecule, a RET acceptor molecule, a PCA bait protein, and a PCA prey protein; b) contacting one or more isolated reporter protein fusion antibody with target molecules together with one or more acceptor antibody, the acceptor antibody comprising an antibody linked to a protein or fragment thereof selected from the group consisting of a RET donor molecule, a RET acceptor molecule, a PCA bait protein, and a PCA prey protein; and c) detecting a detectable signal generated when the reporter protein fusion antibody contacts or is in close proximity to the acceptor antibody.

In one embodiment, one or more reporter protein fusion antibody is isolated from a transgenic animal expressing the one or more reporter protein fusion antibody.

In one embodiment, the invention relates to a method of detecting a target molecule in a sample comprising the step of contacting the target molecule with a first reporter protein fusion antibody; wherein the first reporter protein fusion antibody comprises an antigen-binding domain linked to a reporter protein or fragment thereof, wherein the antigen binding domain is specific for binding to an epitope on the target molecule, and wherein the reporter protein or fragment thereof is a fluorescent protein, a RET donor molecule, a RET acceptor molecule, a PCA bait protein, a PCA prey protein, GFP, HRP, AP, luciferase, β-galactosidase, chloramphenicol acetyl transferase, glucose oxidase, acetate kinase, xanthine oxidase or glucose 6-phosphate dehydrogenase.

In one embodiment, the method further comprises contacting the target molecule with at least one additional antibody. In one embodiment, the at least one additional antibody is specific for binding to an epitope on the same target molecule as the first reporter protein fusion antibody and the binding of the target by the least one additional antibody does not interfere with the binding of the target by the first reporter protein fusion antibody. In one embodiment, at least one additional antibody comprises a reporter protein fusion antibody. In one embodiment, the at least one additional antibody is fused to a fluorescent protein, a RET donor molecule, a RET acceptor molecule, a PCA bait protein, a PCA prey protein, GFP, HRP, AP, luciferase, β-galactosidase, chloramphenicol acetyl transferase, glucose oxidase, acetate kinase, xanthine oxidase, or glucose 6-phosphate dehydrogenase.

In one embodiment, the invention relates to a method of detecting at least two target molecules in close proximity in a sample comprising a) contacting a first target molecule with a first reporter protein fusion antibody, wherein the first reporter protein fusion antibody comprises an antigen-binding domain linked to a reporter protein or fragment thereof, wherein the antigen binding domain is specific for binding to an epitope on the target molecule, and wherein the reporter protein of the first reporter protein fusion antibody is a RET donor molecule, a RET acceptor molecule, a PCA bait protein, or a PCA prey protein, b) contacting a second target molecule with a second antibody linked to a reporter protein or fragment thereof selected from a RET donor molecule, a RET acceptor molecule, a PCA bait protein, or a PCA prey protein, wherein the second antibody comprises an antigen-binding domain specific for binding to an epitope on the second target molecule, and c) detecting a detectable signal generated when the first reporter protein fusion antibody is in close proximity to the second antibody. In one embodiment, the second antibody comprises a reporter protein fusion antibody.

In one embodiment, the invention relates to a method of detecting or diagnosing a disease or disorder in a subject in need thereof, the method comprising the steps of administering to the subject at least one composition comprising a reporter protein fusion antibody, wherein the reporter protein fusion antibody comprises an antigen-binding domain linked to a reporter protein or fragment thereof; and detecting a detectable signal generated from the reporter protein of the reporter protein fusion antibody. In one embodiment, the reporter protein fusion antibody is specific for an antigen associated with a disease or disorder. In one embodiment, the reporter protein fusion antibody is administered to the subject for imaging the distribution of one or more target molecules.

BRIEF DESCRIPTION OF THE DRAWINGS

The following detailed description of exemplary embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 5A and FIG. 5B show the genotyping of exemplary transgenic animals produced by the method of this invention. FIG. 5A is the result of luciferase knock-in at the C end of mouse antibody κ light chain. FIG. 5B is the result of luciferase knock-in at the C end of rabbit antibody κ1 light chain.

FIG. 6A, in contrast to wildtype animal, the transgenic animal contains high reporter enzyme activity in its serum, thus generate strong luminescence signal when the substrate is added. FIG. 6B, the animal responds to antigen (OVA as an example) immunization, and produces antigen specific luciferase fused antibodies that can be used in research and diagnostic immunoassays.

FIG. 15A depicts a plasmid map for a plasmid encoding the HRP-anti-HER2 antibody. A DNA sequence encoding a linker and HRP was inserted before the stop codon of the Igκ. Various length of GGGGS (SEQ ID NO:9) repeating peptide ((G4S)n) were tested. FIG. 15B depicts experimental results demonstrating that when the linker was longer than or equal to 3 repeats of (G4S, n≥3), the fusion protein produced by transfecting the vector in HEK293 cells retains the binding capability to the immobilized HER2 protein, and the fusion protein retaining the HRP enzymatic activity therefore is able to generate a colorimetric signal when supplied with the substrate. When the linker length is shorter than 3 repeats of (G4S, n≤2), either the antibody or HRP cannot be folded correctly so that no signal is detected. FIG. 15C depicts experimental results demonstrating that the fusion protein with longer than or equal to 3 repeats of (G4S, n≥3) linker retains the protein G binding capacity, that can be used for the protein purification. The specificity of the antibody is also retained and no affinity is detected to the immobilized BSA.

FIG. 16A through FIG. 16C depict experimental results demonstrating the in vitro validation of a luciferase fused anti-HER2 antibody. FIG. 16A depicts a plasmid map for a plasmid encoding the luciferase-anti-HER2 antibody. FIG. 16B depicts experimental results demonstrating that when the linker was shorter than or equal to 2 repeats of GGGGS (SEQ ID NO:9) ((G4S)n≤2), the fusion protein produced by transfecting the vector in HEK293 cells retains the binding capability to the immobilized HER2 protein. And the fusion protein retains the luciferase enzymatic activity therefore is able to generate bioluminescent signal when supplied with the substrate. When the linker length is longer than 2 repeats of GGGGS (SEQ ID NO:9) ((G4S)n≥3), either the antibody or luciferase cannot be folded correctly so that no signal is detected. FIG. 16C depicts experimental results demonstrating that the fusion protein with shorter than or equal to 2 repeats of GGGGS (SEQ ID NO:9) ((G4S)n≤3) linker retains the protein G binding capacity, that can be used for the protein purification. The specificity of the antibody is also retained and no affinity is detected to the immobilized BSA.

DETAILED DESCRIPTION

Figure 1:
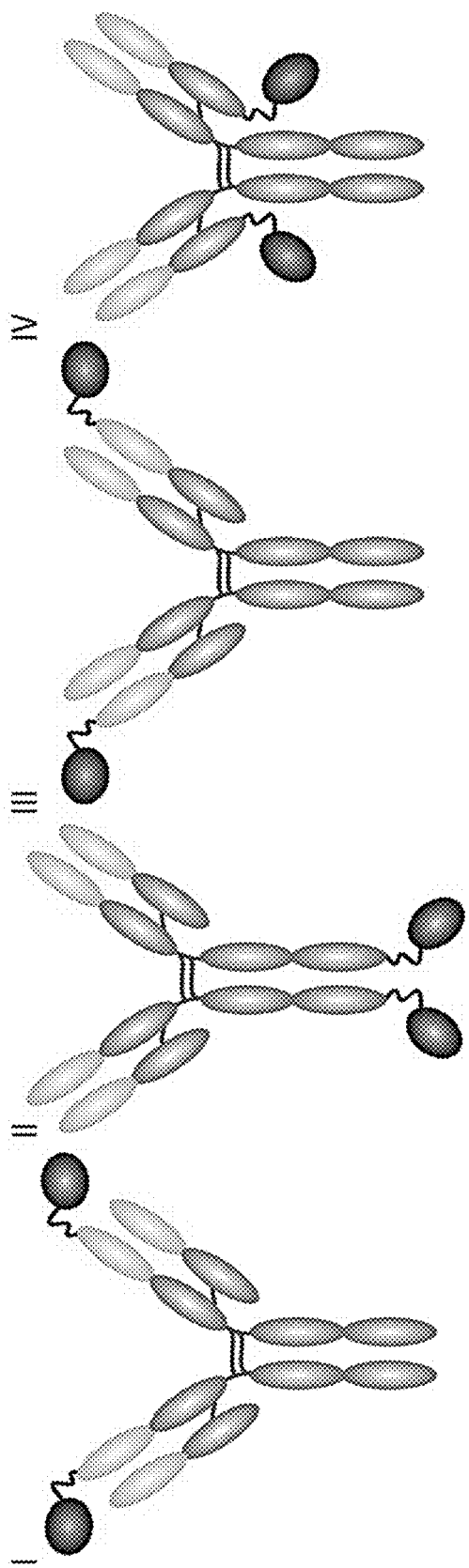
FIG. 1 is a schematic diagram showing the formats of exemplary reporter protein fused antibodies.

The invention, in part, provides methods and materials related to producing reporter protein fused antibodies using transgenic animals. In one embodiment, the reporter protein fused antibodies are generated by knock-in of the reporter protein coding DNA, to fuse with the antibody gene at the corresponding loci through a linker sequence. Such transgenic animals are non-human animals that include but not limited to: non-human primates, rabbits, pigs, birds (e.g., chickens, turkeys, ducks, geese, and the like), sheep, goats, cows, horses, llamas, camels and rodents (e.g. mice and rats). Therefore, in various embodiments, the invention relates to transgenic animals expressing reporter protein antibody fusion proteins.

Fusion sites for the reporter protein or reporter protein fragment on an antibody include: the N terminal of the antibody heavy chain; the C terminal of the antibody heavy chain; the N terminal of the antibody light chain; and the C terminal of the antibody light chain. The fusion protein may form different complexes according to the antibody class. In all cases, the fusion protein should retain the antigen binding capability and be able to generate signal from the reporter protein.

The invention, in part, also provides methods and materials related to an immunoassay using a reporter protein fusion antibody to detect the presence, measure the concentration, and image the distribution of a target molecule both in vitro and in vivo.

The invention, in part, provides methods and materials related to an immunoassay using a pair of antibodies recognizing two different epitopes in close proximity on the same or on different target molecules. One or both antibodies may be fused with a reporter protein to generate the immunoassay signal.

In some embodiments, one or more reporter protein fused antibody is used for antigen detection and quantification. In one embodiment, resonance energy transfer (RET) occurs between two or more reporter genes when brought to close proximity, through binding to their epitopes, to generate a detectable signal. The RET can be fluorescence RET (FRET), in which the donor molecule is excited by an excitation light to activate the donor molecule and generate the signal. The RET can also be bioluminescence RET (BRET), in which the donor molecule is provided with a substrate to generate bioluminescence to activate the donor molecule and generate the signal. In one embodiment, one or more reporter gene fused antibody is fused with a reporter protein fragment (e.g., a protein-fragment complementation assay (PCA) bait protein fragment) which can reconstitute a reporter protein to generate a detectable signal when contacted with a second reporter protein fragment (e.g., a PCA prey protein fragment).

The invention, in part, also provides methods and materials related to screening pairing antibodies recognizing two different epitopes in close proximity on the same or on different target molecules. In the method a first antibody will be used as a bait, to identify the second antibody from the described transgenic animal's natural immune repertoire. Antibody pairs are identified by the RET or PCA signal generated by the close proximity of the two antibodies.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

As used herein, "antigen-binding domain" means that part of the antibody, recombinant molecule, the fusion protein, or the immunoconjugate of the invention which recognizes the target or portions thereof.

The terms "biomarker" and "marker" are used herein interchangeably. They refer to a substance that is a distinctive indicator of a biological process, biological event and/or pathologic condition, disease or disorder.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

The term "detecting" or "detection," means assessing the presence, absence, quantity or amount of a given substance (e.g., a DTC or DTC marker) within a clinical or subject-derived sample, including the derivation of qualitative or quantitative levels of such substances, or otherwise evaluating the values or categorization of a subject's clinical parameters.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, "fragment" is defined as at least a portion of the variable region of the immunoglobulin molecule which binds to its target, i.e. the antigen binding region. Some of the constant region of the immunoglobulin may be included.

As used herein, "fused" means to couple directly or indirectly one molecule with another by whatever means, e.g., by covalent bonding, by non-covalent bonding, by ionic bonding, or by non-ionic bonding. Covalent bonding includes bonding by various linkers such as thioether linkers or thioester linkers. Direct fusion involves one molecule attached to the molecule of interest. Indirect fusion involves one molecule attached to another molecule which in turn is attached directly or indirectly to the molecule of interest.

As used herein, an "immunoconjugate" means any immunoglobulin molecule or fragment thereof such as an antibody or antibody fragment chemically or biologically linked to another agent, for example, a cytotoxin, a radioactive agent, an anti-tumor drug or a therapeutic agent. The antibody or antibody fragment may be linked to the other agent at any location along the molecule so long as it is able to bind its target. Examples of immuoconjugates include antibody conjugates and antibody fragment conjugates.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "nucleic acid" is meant to include any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). The term "nucleic acid" typically refers to large polynucleotides.

As used herein, the terms "peptide," "polypeptide," and "protein" are used interchangeably, and refer to a compound comprising amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein, is meant a molecule, such as an antibody, which recognizes and binds to another molecule or feature, but does not substantially recognize or bind other molecules or features in a sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention provides compositions comprising reporter protein fusion antibody constructs, methods of production thereof, and methods of use of the same. In various embodiments, the methods of use of the reporter protein fusion antibody constructs include, but are not limited to, immunoassays and methods for generation and use of transgenic animals expressing the reporter protein fusion antibody constructs of the invention.

Compositions

The present disclosure relates to reporter protein fusion antibody compositions, nucleic acid molecules encoding the same, and also to cells, tissues, or transgenic animals expressing the reporter protein fusion antibodies of the invention.

Reporter Protein Antibody Fusion Proteins

In one embodiment, the invention provides reporter protein fusion antibodies. Reporter protein fusion antibodies of the invention comprise an antigen-binding domain, which recognizes a specific epitope or antigen of a targeting molecule, fused to a reporter gene or a fragment thereof.

The antigen-binding domain of the reporter protein fusion antibodies recognizes and specifically binds to an antigen, such as a protein, polypeptide, peptide, carbohydrate, polynucleotide, and lipid. In one embodiment, the antigen-binding domain of the reporter protein fusion antibody may be an antibody fragment, including but not limited to Fab, Fab', F(ab')2, and Fv fragments. In one embodiment, the antigen-binding domain of the reporter protein fusion antibody is specific for an epitope of a target molecule.

In one embodiment, the antibody specifically binds to a target or protein of interest. Antibodies are capable of "specific binding" to a particular target or series of antigenically related targets. As used herein, an antibody is said to be capable of "specific binding" to an antigen if it discriminates from antigenically distinct molecules based on binding of those molecules to the variable region of the antibody. Such interactions are in contrast to non-specific binding that involve classes of compounds, irrespective of their chemical structure (such as the binding of proteins to nitrocellulose, etc.).

Such antibodies include polyclonal antibodies, monoclonal antibodies, Fab and single chain Fv (scFv) fragments thereof, bispecific antibodies, heteroconjugates, and human and humanized antibodies. Such antibodies may be produced in a variety of ways, including hybridoma cultures, recombinant expression in bacteria or mammalian cell cultures, and recombinant expression in transgenic animals. The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments (such as Fab and Fv fragments), as well as chimeric antibodies comprising components from different species.

The antibodies of the present invention may be polyclonal antibodies. Such polyclonal antibodies can be produced in a mammal, for example, following one or more injections of an immunizing agent, and in some embodiments, an adjuvant. Typically, the immunizing agent and/or adjuvant will be injected into the mammal by a series of subcutaneous or intraperitoneal injections. The immunizing agent may include a positive or negative selection marker of the invention or a fragment thereof. Alternatively, a crude protein preparation which has been enriched for a positive or negative selection marker or a fragment thereof can be used to generate antibodies. Such proteins, fragments or preparations are introduced into the non-human mammal in the presence of an appropriate adjuvant. If the serum contains polyclonal antibodies to undesired epitopes, the polyclonal antibodies are purified by immunoaffinity chromatography.

Alternatively, the antibodies may be monoclonal antibodies. Monoclonal antibodies may be produced by hybridomas, wherein a mouse, hamster, or other appropriate host animal is immunized with an immunizing agent to elicit lymphocytes that produce or are capable of producing antibodies that will specifically bind to the immunizing agent, e.g. Kohler and Milstein, Nature 256:495 (1975). The immunizing agent will typically include a positive or negative selection marker or a fragment thereof and optionally a carrier. Alternatively, lymphocytes may be immunized in vitro. Generally, spleen cells or lymph node cells are used if non-human mammalian sources are desired, or peripheral blood lymphocytes ("PBLs") are used if cells of human origin are desired. The lymphocytes are fused with an immortalized cell line using a suitable fusing agent, such as polyethylene glycol, to produce a hybridoma cell. In general, immortalized cell lines are transformed mammalian cells, for example myeloma cells of rat, mouse, bovine, or human origin. The hybridoma cells are cultured in a suitable culture medium that can contain one or more substances that inhibit the growth or survival of unfused, immortalized cells. The culture medium (supernatant) in which the hybridoma cells are cultured can be assayed for the presence of monoclonal antibodies directed against a positive or negative selection marker by conventional techniques, such as by immunoprecipitation or by an in vitro binding assay, such as RIA or ELISA.

The monoclonal antibodies may also be made by recombinant DNA methods, such as those described in U.S. Pat. No. 4,816,567. DNA encoding the monoclonal antibodies of the invention can be isolated from the positive or negative selection marker specific hybridoma cells and sequenced, e.g., by using oligonucleotide probes that are capable of binding specifically to genes encoding the heavy and light chains of murine antibodies. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA may also be modified, for example, by substituting the coding sequence for the murine heavy and light chain constant domains for the homologous human sequences, or by covalently joining to the immunoglobulin coding sequence all or part of the coding sequence for a non-immunoglobulin polypeptide. The non-immunoglobulin polypeptide can be substituted for the constant domains of an antibody of the invention, or can be substituted for the variable domains of one antigen-combining site of an antibody of the invention to create a chimeric bivalent antibody.

The antibodies may also be monovalent antibodies. Methods for preparing monovalent antibodies are well known in the art. For example, in vitro methods are suitable for preparing monovalent antibodies. Digestion of antibodies to produce fragments thereof, particularly for example Fab fragments, can be accomplished using routine techniques known in the art.

Antibodies and antibody fragments characteristic of hybridomas of the invention can also be produced by recombinant means by extracting messenger RNA, constructing a cDNA library, and selecting clones which encode segments of the antibody molecule.

The antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F(ab'), or other antigen-binding partial sequences of antibodies) which contain some portions of the sequence derived from non-human antibodies. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody can comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Methods for humanizing non-human antibodies are well known in the art. Generally, a humanized antibody has one or more amino acids introduced into it from a source which is non-human in order to more closely resemble a human antibody, while still retaining the original binding activity of the antibody.

Heteroconjugate antibodies which comprise two covalently joined antibodies, are also within the scope of the present invention. Heteroconjugate antibodies may be prepared in vitro using known methods in synthetic protein chemistry, including those involving crosslinking agents. For example, immunotoxins may be prepared using a disulfide exchange reaction or by forming a thioether bond.

In one embodiment, the antibodies of the invention can be "chimeric antibodies" as that term is recognized in the art. As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially advantageous in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L. et al., Proc. Nat'l Acad. Sci., 81, 6851 (1984).

Encompassed by the term "chimeric antibody" is the concept of "humanized antibody", that is those antibodies in which the framework or "complementarity" determining regions ("CDR") have been modified to comprise the CDR of an immunoglobulin of different specificity as compared to that of the parent immunoglobulin. In certain embodiments, a murine CDR is grafted into the framework region of a human antibody to prepare the "humanized antibody". See, e.g., L. Riechmann et al., Nature 332, 323 (1988); M. S. Neuberger et al., Nature 314, 268 (1985). Particular CDR'S correspond to those representing sequences recognizing the antigens noted above for the chimeric antibodies.

Reporter Gene

In one embodiment, the reporter protein fusion antibody comprises at least one reporter molecule, or a fragment thereof. A number of reporter proteins can be incorporated as the reporter into a reporter protein fusion antibody of the invention, including, but not limited to, fluorescence proteins, green fluorescence protein (GFP) and variants thereof, horseradish peroxidase (HRP), alkaline phosphatase (AP), luciferase, firefly luciferase, Renilla luciferase, and deep sea shrimp luciferase and variants thereof, β-galactosidase, chloramphenicol acetyl transferase, glucose oxidase, acetate kinase, xanthine oxidase, and glucose 6-phosphate dehydrogenase.

The reporter protein can be fused to any site on an antibody, so long as the fusion does not disrupt the binding of the antibody to its target. The reporter protein can be fused to the N terminal of the antibody heavy chain, the C terminal of the antibody heavy chain, the N terminal of the antibody light chain, or the C terminal of the antibody light chain. The reporter protein gene can be inserted at the N terminal of a heavy or light chain, following the ATG start codon. The reporter protein gene can also be inserted at the C terminal of a heavy or light chain, before the stop codon.

In one embodiment, an antibody light chain can be a κ or λ chain (Igκ or Igλ.) In one embodiment, an antibody heavy chain can be a γ-chain, a μ-chain, δ-chain, α-chain, or ε-chain (IgG, IgM, IgD, IgA, or IgE.)

The reporter protein can be the donor or acceptor of a fluorescence resonance energy transfer (FRET) pair, examples including but are not limited to CFP-YFP, EGFP-mCherry, Venus-mCherry, Venus-tdTomato, Venus-mPlum, EBFP2-mEGFP, MiCy-mKO, TFP1-mVenus, and CyPet-YPet. The reporter protein can also be the donor or acceptor of the bioluminescence resonance energy transfer (BRET) pair, examples including but are not limited to RLuc-EYFP, RLuc-Topaz, RLuc-GFP, Aequorin-GFP, firefly luciferase-RFP, and NanoLuc-HaloTag.

The reporter protein fragment fused to the antibody can be either the N or C terminal half of the reporter protein. In such an embodiment, the N and C terminal halves of a reporter protein can serve as the prey and bait proteins of a protein fragment complementation assay, in which a detectable signal is generated with the N and C terminal halves contact each other to reconstitute the activity of the reporter protein. Examples of reporter proteins that can be split in halves and reconstitute the activity through complementation include but are not limited to HRP, GFP, luciferase and its variants, β-lactamase, dihydrofolate reductase, focal adhesion kinase, Gal4, infrared fluorescent protein IFP1.4, β-galactosidase, tobacco etch virus protease, and ubiquitin.

In choosing the reporter protein the secretion and folding requirements of antibodies and reporter proteins have to be compatible. Some proteins, such like GFP and YFP, may not fold effectively and properly in the endoplasmic reticulum (ER) in which antibodies are folded.

Linker

In one embodiment, a linker sequence is used to link a reporter protein to an antibody. In one embodiment, the linker sequence is selected such that the functions of both the antibody and the reporter protein are retained. Exemplary linkers that may be used in the compositions and methods of the invention include, but are not limited to, linkers such as (GGGGS)$_2$ (SEQ ID NO:10), (GGGGS)$_3$ (SEQ ID NO:11), (GGGGS)$_4$ (SEQ ID NO:12), (GGGGS)$_5$ (SEQ ID NO:13), and other linkers known in the art.

Modifications of the Reporter Protein Fusion Antibodies

In one embodiment the reporter protein fusion antibody is modified. Modifications that are contemplated for use in the reporter protein fusion antibodies of the invention include, but are not limited to disulfide bond formation, glycosylation, lipidation, acetylation, phosphorylation, or any other manipulation or modification, such as conjugation. Also included are, for example, mutation to cysteine for thiol-mediated conjugation or incorporation of one or more analogs of an amino acid (including, for example, unnatural amino acids, etc.). An "unnatural amino acid" is, in this case a molecule containing a primary amine functionality and carboxylic acid functionality that can be incorporated into a protein primary sequence with a transferable atom or group that is completely incorporated into the final product. In one embodiment, the unnatural amino acid is site-specifically incorporated into the immunoconjugate molecule. A general method of preparing a protein with a site-specifically incorporated unnatural amino acid is disclosed by Mehl et al., PCT/US2011/57043, and is incorporated herein by reference.

In one embodiment, the reporter protein fusion antibody comprises one or more non-naturally encoded amino acid. A very wide variety of non-naturally encoded amino acids are suitable for use in the present invention. Any number of non-naturally encoded amino acids can be introduced into the reporter protein fusion antibody of the invention. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). Non-naturally encoded amino acids can form amide bonds with other amino acids, including but not limited to, natural or non-naturally encoded, in the same manner in which they are formed in naturally occurring polypeptides. However, non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Non-naturally occurring amino acids that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiple substituted aryl rings are also contemplated. Glutamine analogs that may be suitable for use in the present invention include, but are not limited to, alpha-hydroxy derivatives, gamma-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent includes but is not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc.beta.-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, a p-propargyloxy-phenylalanine, a p-azido-L-phenylalanine (pAzF), a p-iodo-phenylalanine, a p-bromophenylalanine, a p-amino-L-phenylalanine, and the like. In one embodiment, a non-naturally encoded amino acid for use in the invention is p-acetylphenylalanine (pAcF).

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Certain isotopically-labelled compounds described herein, for example those into which radioactive isotopes such as $^3$H and $^{14}$C are incorporated, may be useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

Nucleic Acid Molecules

In some embodiments, the composition of the invention comprises an isolated nucleic acid molecule encoding one or more reporter protein fusion antibody as described herein. In some embodiments, the composition of the present invention comprises one or more vectors comprising a coding sequences for expression of one or more reporter protein fusion antibody described herein. Vectors allow or facilitate the transfer of an entity from one environment to another. It is a replicon, such as a plasmid, phage, or cosmid, into which another DNA segment may be inserted so as to bring about the replication of the inserted segment. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

In some embodiments, a vector comprises one or more regulatory elements. Regulatory elements include those that direct constitutive expression of a nucleotide sequence in many types of host cell and those that direct expression of the nucleotide sequence only in certain host cells (e.g., tissue-specific regulator sequences). In various embodiments, the vector comprises one or more promoters, enhancers, internal ribosomal entry sites (IRES), and other expression control elements (e.g. transcription termination signals, such as polyadenylation signals and poly-U sequences) and enhancer elements (e.g., WPRE; CMV enhancers; and the SV40 enhancer.) Examples of promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., proteins, enzymes, mutant forms thereof, fusion proteins thereof, etc.).

Vectors may be introduced and propagated in a prokaryote or prokaryotic cell, in some embodiments, a prokaryote is used to amplify copies of a vector to be introduced into a eukaryotic cell or as an intermediate vector in the production of a vector to be introduced into a eukaryotic ceil (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pR(T5 (Pharmacia, Piscataway, N.J.) that fuse glutathione S-transferase (GST), maltose E binding protein, or protein A, respectively, to the target recombinant protein. In some embodiments, a vector is a yeast expression vector. Examples of vectors for expression in yeast *Saccharomyces cerivisae* include pYepSecl (Baldari, et al., 1987. EMBO J. 6: 229-234), pMFa (uijan and Herskowitz, 1982. Cell 30: 933-943), pJRY88 (Schultz et al, 1987. Gene 54: 1 13-123), pYES2 (Invitrogeii Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 4th ed., Cold Spring Harbor Laboratory, Cold Spring Harbor Laboratory Press, Cold Spring Harbor, N.Y., 2012.

In some embodiments, the recombinant mammalian expression vector is capable of directing expression of the nucleic acid in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Caiame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Grass, 1990. Science 249: 374-379) and the a-fetoprotein promoter (Campes and Tilghman, 1989. Genes Dev. 3: 537-546). With regards to these pro-karyotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. Tissue specific promoters, for expression of the reporter protein fusion antibodies, may be used for tissue-specific targeting, thus providing spatial control. Different tissue specific promoters may be used to exert a finer degree of control if required. The same approach may be used in respect of stage-specific promoters or there may a mixture of stage and tissue specific promoters.

In some embodiments, the composition comprises one or more vectors encoding one or more reporter protein fusion antibodies described herein. For example, in one embodiment, a first reporter protein fusion antibody, wherein the reporter gene comprises a FRET donor, and a second reporter protein fusion antibody, wherein the reporter gene comprises a FRET acceptor could each be operably linked to separate regulatory elements on separate vectors. Alternatively, two or more reporter protein fusion antibodies may be expressed from the same or different regulatory elements, on a single vector.

Biosensors

In one embodiment, the compositions of the invention are used as biosensors, e.g. with sensor systems with amperometric, electrochemical, potentiometric, conductimetric, impedance, magnetic, optical, acoustic or thermal transducers.

Generally, biosensors include a biosensor recognition element which can include proteins, nucleic acids, antibodies, etc. that bind to a particular biomarker or compound and a transducer which converts a molecular signal (i.e. binding of biomarker to recognition element) into an electric or digital signal that can be quantified, displayed, and analyzed. Biosensors may also include a reader device which translates the signal into a user-friendly display of the results. Examples of potential components that comprise an exemplary biosensor are described in Bohunicky et al. (2011, Nanotechnology Science and Applications, 4: 1-10), which is hereby incorporated by reference in its entirety.

A biosensor may incorporate a physical, chemical or biological detection system. In one embodiment, a biosensor is a sensor with a biological recognition system, e.g. based on a nucleic acid, such as an oligonucleotide probe or aptamer, a protein such as an enzyme, binding protein, receptor protein, transporter protein or antibody (e.g., a reporter gene antibody fusion). In one embodiment, the biological recognition system may comprise traditional immunoassays described elsewhere herein. In another element, binding of the biomarker to the recognition element (e.g reporter gene antibody fusion) is directly observed and converted into a signal by a transducer.

The method for detection of the biomarker or compound in a biosensor may comprise immunological, electrical, thermal, magnetic, optical (e.g. hologram) or acoustic technologies. Using such biosensors, it is possible to detect the target biomarker or compound at the anticipated concentrations found in biological samples.

The biosensor may incorporate detection methods and systems as described herein for detection of the biomarker or compound. Biosensors may employ electrical (e.g. amperometric, potentiometric, conductimetric, or impedance detection systems), calorimetric (e.g. thermal), magnetic, optical (e.g. hologram, luminescence, fluorescence, colorimetry), or mass change (e.g. piezoelectric, acoustic wave) technologies. In a biosensor, according to the invention the level of one, two, three, or more biomarkers can be detected by one or more methods selected from: direct, indirect or coupled enzymatic, spectrophotometric, fluorimetric, luminometric, spectrometric, polarimetric, and chromatographic techniques. In some embodiments, biosensors comprise one or more enzymes used directly or indirectly via a mediator, or using a binding, receptor or transporter protein, coupled to an electrical, optical, acoustic, magnetic, or thermal transducer. Using such biosensors, it is possible to detect the level of target biomarkers at the anticipated concentrations found in biological samples.

In one embodiment of a biosensor, one or more biomarkers or compounds of the invention can be detected using a biosensor incorporating technologies based on "smart" holograms, or high frequency acoustic systems, such systems are particularly amenable to "bar code" or array configurations. In smart hologram sensors (Smart Holograms Ltd, Cambridge, UK), a holographic image is stored in a thin polymer film that is sensitized to react specifically with the biomarker or compound. On exposure, the biomarker or compound reacts with the polymer leading to an alteration in the image displayed by the hologram. The test result read-out can be a change in the optical brightness, image, color and/or position of the image. For qualitative and semi-quantitative applications, a sensor hologram can be read by eye, thus removing the need for detection equipment. A simple color sensor can be used to read the signal when quantitative measurements are required. Opacity or color of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Biosensors to detect one or more biomarkers, compounds, or the proximity of multiple compounds using the reporter protein fusion antibodies of the present invention may include acoustic, surface plasmon resonance, holographic and microengineered sensors. Imprinted recognition elements, thin film transistor technology, magnetic acoustic resonator devices and other novel acousto-electrical systems may be employed in biosensors for detection of the biomarkers or compounds of the invention.

Suitably, biosensors for detection of one or more biomarkers or compounds of the invention are coupled, i.e. they combine biomolecular recognition with appropriate means to convert detection of the presence, or quantitation, of the biomarker or compound in the sample into a signal. Biosensors can be adapted for "alternate site" diagnostic testing, e.g. in the ward, outpatients' department, surgery, home, field and workplace.

Methods involving detection and/or quantification of the biomarker or compound of the invention can be performed using bench-top instruments, or can be incorporated onto disposable, diagnostic or monitoring platforms that can be used in a non-laboratory environment, e.g. in the physician's office or at the patient's bedside.

Methods of Detection

In one embodiment, the invention provides methods for detecting the presence, concentration, or proximity of one or more target molecules in a sample using the reporter protein fusion antibodies of the invention. The presence, concentration, or proximity of one or more compounds in a sample may be determined by any suitable assay. In one embodiment, a suitable assay is an immunoassay or proximity assay. As used herein, an "immunoassay" refers to any binding assay that uses an antibody capable of binding specifically to a target molecule to detect and quantify the target molecule. In various embodiments of the invention, immunoassays that can be performed using a reporter protein fusion antibody of the invention include, but are not limited to, an immunochromatography assay, an immunodot assay, a lateral flow assay, a Luminex assay, an ELISA assay, an ELISPOT assay, a protein microarray assay, a ligand-receptor binding assay, displacement of a ligand from a receptor assay, displacement of a ligand from a shared receptor assay, an immunostaining assay, a Western blot assay, a radioimmunoassay (RIA), a radioimmunodiffusion assay, an ouchterlony immunodiffusion assay, a rocket immunoelectrophoresis assay, an immunohistostaining assay, an immunoprecipitation assay, FACS, an enzyme-substrate binding assay, an enzymatic assay, a substrate binding assay, a substrate displacement assay, and other assays in which antibodies are used (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005).

The invention described herein also relates to methods for a multiplex analysis platform. In one embodiment, the method comprises an analytical method for multiplexing analytical measurements of markers.

In one embodiment, the sample of the invention is a biological sample. The biological sample can originate from solid or fluid samples. The sample of the invention may comprise urine, whole blood, blood serum, blood plasma, cerebrospinal fluid, lymph, bronchial aspirates, milk, sweat, tears, skin, hair, saliva, and the like.

In some embodiments, the sample is a laboratory sample. In some embodiments, the sample is a tissue culture sample, or cell lysate.

Methods of Generating Reporter Protein Antibody Fusion Proteins

In one embodiment, a transgenic animal is generated by gene knock-in, with a targeting vector encoding a reporter protein fusion antibody and appropriate homology arms to achieve homologous recombination of the vector into the genome. The targeting vector can be administered into a cell by any appropriate means including, but not limited to, microinjected into the pronuclei of a fertilized egg, or transfected into embryonic stem cells and then microinjected into an embryo at the blastocyst stage of development. In one embodiment, the fertilized egg or blastocyst is then implanted into the oviduct of a pseudopregnant surrogate mother to produce the knock-in transgenic animals.

In one embodiment, the targeting vector contains a nucleotide sequence as set forth in SEQ ID NO:1 to knock-in a HRP gene at the C end of mouse κ light chain. In one embodiment, the targeting vector contains a nucleotide sequence as set forth in SEQ ID NO:2 to knock-in a HRP gene at the C end of rabbit κ1 light chain. In one embodiment, the targeting vector contains a nucleotide sequence as set forth in SEQ ID NO:3 to knock-in a NanoLuc gene at the C end of mouse κ light chain. In one embodiment, the targeting vector contains a nucleotide sequence as set forth in SEQ ID NO:4 to knock-in a NanoLuc gene at the C end of rabbit κ1 light chain.

In one embodiment, the reporter protein antibody fusion protein can be produced in vitro, by introducing the coding DNA into the expressing cells. The expressing cell can be prokaryotic cells such as E. coli, eukaryotic cells such as yeast and mammalian cells. The reporter protein antibody fusion protein can also be produced in vivo in transgenic animals, by knock-in the reporter protein coding DNA, to fuse with the antibody gene at the corresponding loci through a linker sequence. Such transgenic animals are non-human animals include, but not limited to non-human primates, rabbits, pigs, birds (e.g., chickens, turkeys, ducks, geese and the like), sheep, goats, cows, llamas, camels, horses, and rodents (e.g. mice and rats). Exemplary non-human animals are those animals that are commonly used for antibody production, e.g., mouse, rabbit, rat, goat, donkey, chicken, cow, llama and camel.

Anti-VEGFA Reporter Protein Fusion Antibody

In one embodiment, the reporter protein fusion antibodies of the invention can be used for detection of a target or modifying a given biological response of a disease or disorder.

In one aspect, the antibodies of the present invention are useful for detecting, diagnosing, treating or preventing a disease or disorder associated with a targeted antigen. In one embodiment, antibodies of the invention can be used diagnostically to monitor protein levels in a sample as part of a clinical testing procedure, e.g., to determine the efficacy of a given treatment regimen.

Therefore, the reporter protein fusion antibody is not to be construed as limited to any specific type of antibody. Rather, any antibody possessing a desired biological activity may be fused with a reporter gene to form a reporter protein fusion antibody of the invention. Exemplary antibodies may include, for example, antibodies used for detection or treatment of a disease or disorder.

An exemplary reporter protein fusion antibody produced by the method of the invention includes, but is not limited to, an anti-VEGFA antibody wherein the C terminus of the light chain of the antibody is fused to a reporter gene encoding HRP. In one embodiment, the reporter protein fusion anti-VGFA antibody comprises a heavy chain sequence as set forth in SEQ ID NO:5 and a light chain sequence as set forth in SEQ ID NO:7. In one embodiment, the reporter protein fusion anti-HER2 antibody comprises a heavy chain sequence encoded by a nucleotide sequence as set forth in SEQ ID NO:6 and a light chain sequence encoded by a nucleotide sequence as set forth in SEQ ID NO:8.

Analysis Methods

In some embodiments, the methods of the invention include performing an assay using a reporter protein fusion antibody of the invention. In one embodiment, the invention includes the use of a reporter protein fusion antibody in any bioassay that can be used to determine the level or concentration of at least one target protein or biomarker. For example, one or more reporter protein fusion antibody can be used to analyze and determine the presence or absence of at least one protein or biomarker in a sample. In one embodiment, a biological sample is contacted with one or more reporter protein fusion antibody to determine the concentration or level of expression of the at least one protein or biomarker in the sample. Immunoassay methods are suitable in this regard and may be carried out in any of a wide variety of formats. Immunological assay methods generally involve a reagent capable of specifically binding a marker. Suitable immunologic methods include, but are not limited to, a lateral flow assay, immunoprecipitation, particle immunoassay, immunonephelometry, radioimmunoassay (MA), enzyme immunoassay (EIA) including enzyme-linked immunosorbent assay (ELISA), sandwich, direct, indirect, or competitive ELISA assays, enzyme-linked immunospot assays (ELISPOT), multiplex ELISA array, fluorescent immunoassay (FIA), chemiluminescent immunoassay, flow cytometry assays, immunohistochemistry, Western blot, integrated blood barcode chip and protein-chip assays using for example the antibody or fragment thereof of the invention. In one embodiment, the invention includes the use of a reporter protein fusion antibody in any bioassay that can be used to image the target protein or biomarker in vivo, in live animals or human subject.

In one embodiment, once measured, the concentration of each biomarker and that of any other additional biomarker being assessed is compared to a predetermined reference value for the specific biomarker. The reference value may be determined in one of several ways. For example, the marker reference value can be the marker concentration measured in a sample taken from a control subject, or may be the median marker concentration calculated from the concentrations measured in multiple control samples taken from a group of control subjects.

Screening Methods

In one embodiment, the invention provides a screening method for identification of reporter protein fused antibodies that can serve as emission donors (e.g., FRET donors) for use in proximity assays. In one embodiment, a first reporter protein fused antibody, wherein the reporter protein is a donor molecule is generated (e.g. isolated from a transgenic animal expressing the first reporter protein). A second antibody is either also produced from a transgenic animal and fused with an acceptor reporter protein; or produced as a traditional mAb and chemically conjugated with an acceptor molecule; or in vitro expressed in cells as an acceptor reporter protein fused antibody. In one embodiment, the second antibody with an acceptor molecule is used as the screening probe. In some implementations, the probe can first be validated by reaction with the antigen, and the donor reporter protein fused pAb generated from the immunized transgenic animals. RET or PCA signals are measured and the acceptor antibody generating strong signals are used as the screening probe.

mAb expressing cells, either hybridoma or other cultured cells, are generated from the transgenic animals of the invention to generate a library. Supernatants containing donor reporter protein fused mAbs are collected, then incubated with the antigen and the screening probe to measure the RET or PCA signal. Pairs of mAb donor and acceptor are established from screening the clones generating strong signals.

Proximity Assay

In one embodiment, the invention provides methods for using two or more reporter protein fused antibodies of the invention for detecting the presence and concentration of target molecules. Signals are generated when the two reporter fusion antibodies of the invention bind to different epitopes on the same target molecule in close proximity (i.e., a proximity assay). In some implementations, a first reporter protein serves as a PCA bait protein, and a second reporter protein serves as a PCA prey protein, and a detectable signal is generated when PCA bait protein and PCA prey protein come into contact to reconstitute a reporter protein. In some implementations, a first reporter protein serves as a resonance energy transfer donor molecule, and a second reporter protein serves as a resonance energy transfer acceptor molecule, and a detectable signal is generated when the first reporter protein fusion antibody is in close proximity to the second reporter protein fusion antibody. The antigen detection and quantification are measured by the resonance energy transfer between two reporter proteins. Examples of resonance energy transfer that can occur include, but are not limited to, fluorescence resonance energy transfer (FRET), and bioluminescence resonance energy transfer (BRET). In one embodiment, a donor reporter protein and an acceptor reporter protein are in close proximity when the donor and acceptor are less than 15 nm apart, less than 14 nm apart, less than 13 nm apart, less than 12 nm apart, less than 11 nm apart, less than 10 nm apart, less than 9 nm apart, less than 8 nm apart, less than 7 nm apart, less than 6 nm apart, less than 5 nm apart, less than 4 nm apart, less than 3 nm apart, less than 2 nm apart, or less than 1 nm apart.

In one embodiment, the invention provides methods for using one or more reporter protein fusion antibodies of the invention for detection of a proximal spatial relationship between two or more target molecules (i.e., a proximity assay). In some implementations, the reporter is fused as a complete functional protein to the antibody, and is brought to proximity with another signal generating molecule through binding to the antigen in a homogenous immunoassay. For example, in one embodiment, a first target molecule is contacted with a first reporter protein fusion antibody of the invention, a second target molecule is contacted with a second reporter protein fusion antibody of the invention, and a detectable signal is generated when the first reporter protein fusion antibody contacts the second reporter protein fusion antibody. In one embodiment, a first target molecule is contacted with a reporter protein fusion antibody of the invention, wherein the reporter protein serves as a PCA bait protein, and a second target molecule is contacted with an antibody comprising a PCA prey protein, and a detectable signal is generated when PCA bait protein and PCA prey protein come into contact to reconstitute a reporter protein, allowing for the generation of a detectable signal.

In one embodiment, a first target molecule is contacted with a reporter protein fusion antibody of the invention, wherein the reporter protein serves as a resonance energy transfer donor molecule, and a second target molecule is contacted with an antibody comprising a resonance energy transfer acceptor molecule, and a detectable signal is generated when the first reporter protein fusion antibody is in close proximity to the second antibody. In one embodiment, the second antibody is a second reporter protein fusion antibody. The antigen detection and quantification are measured by the resonance energy transfer between the reporter protein of the first reporter protein fusion antibody and the acceptor protein bound to the proximate molecule. Examples of resonance energy transfer that can occur include, but are not limited to, fluorescence resonance energy transfer (FRET), and bioluminescence resonance energy transfer (BRET). In one embodiment, a reporter protein fusion antibody of the invention is in close proximity to a, for example, when the two or more target molecules are close enough that an emission by a donor reporter protein of a reporter protein fusion antibody can be accepted by an acceptor reporter protein. In one embodiment, a donor reporter protein and an acceptor reporter protein are in close proximity when the donor and acceptor are less than 15 nm apart, less than 14 nm apart, less than 13 nm apart, less than 12 nm apart, less than 11 nm apart, less than 10 nm apart, less than 9 nm apart, less than 8 nm apart, less than 7 nm apart, less than 6 nm apart, less than 5 nm apart, less than 4 nm apart, less than 3 nm apart, less than 2 nm apart, or less than 1 nm apart.

Kits

The present invention also pertains to kits useful in the methods of the invention. Such kits comprise various combinations of components useful in any of the methods described elsewhere herein, including for example, a reporter protein fusion antibody, and instructional material. For example, in one embodiment, the kit comprises components useful for the detection of a target molecule in a sample. In another embodiment, the kit comprises components useful for the detection of the proximity of two or more molecules in a sample.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Example 1: Proximity Immunoassay Using Reporter Protein Fused Antibodies

FIG. 1 illustrates the possible fusion site for the reporter protein on an antibody, including (I) the N terminal of the antibody heavy chain; (II) the C terminal of the antibody heavy chain; (III) the N terminal of the antibody light chain; and (IV) the C terminal of the antibody light chain. Shown in FIG. 1 is a monomer IgG as an example. Other classes of antibodies may form different complexes, such like the IgA dimer and IgM pentamer. The fusion protein may form different complexes according to the antibody class. In all cases the fusion protein should retain the antigen binding capability and able to generate signal from the reporter protein.

This example provides the concept, design and methods related to the transgenic animals producing reporter protein fused antibodies. The example specifically relates to the design of knock-in loci to fuse the reporter protein to immunoglobulin genes, the method for validating the reporter protein and linker sequence in vitro, the method for genotyping the transgenic animals, the method for immunizing the transgenic animals, and the method for using the transgenic animal produced reporter enzyme fused antibodies in immunoassays.

This document provides methods and materials related to transgenic animals producing reporter protein fused antibodies. The animals are non-human animals include, but not limited to non-human primates, rabbits, pigs, birds (e.g., chickens, turkeys, ducks, geese and the like), sheep, goats, cows, llamas, camels, horses, and rodents (e.g. mice and rats). Exemplary non-human animals include, but are not limited to, animals that are commonly used for antibody production, e.g., mouse, rat, dog, rabbit, pig, guinea pig, donkey, sheep, a goat, chicken, cow, llama and camel.

Figure 2:
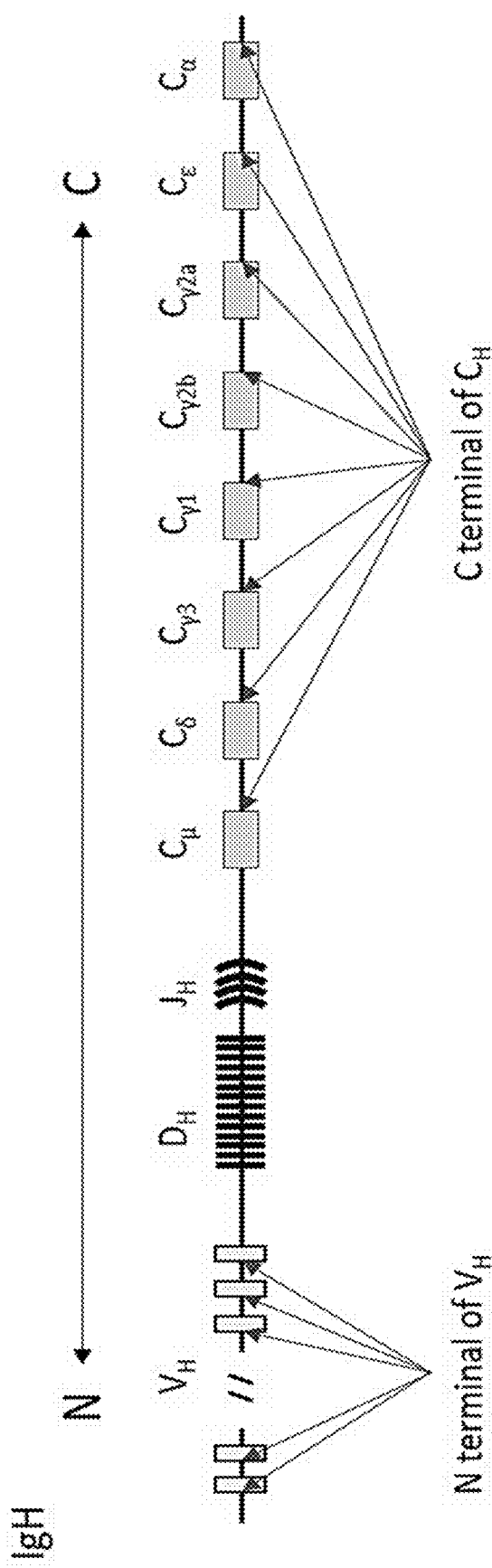
FIG. 2 is a schematic diagram showing exemplary gene fusion sites on the immunoglobulin heavy chain gene (IgH).

FIG. 2 illustrates the method to fuse the reporter protein gene to the antibody heavy chain (IgH) genes. The reporter protein gene can be inserted at the N terminal of the V gene of the heavy chain (VH), following the ATG start codon. Animals may contain various numbers of VH genes depending on the species and strains. The reporter gene can be inserted following the ATG start codon of any one of, or any combination of these genes. The reporter protein gene can also be inserted at the C terminal of the constant gene of the heavy chain (CH), but before the stop codon of CH. Animals contain various CH genes to produce different classes and subclasses of antibodies, such like the IgG1, IgG2, IgG3, IgM, IgD, IgE, and IgA in mice. These constant regions of these antibodies are coded by the Cγ1, Cγ2, Cγ3, Cμ, Cδ, Cε, and Cα in mice as shown in FIG. 2. The reporter gene can be inserted before the stop codon of any one of, or any combination of these genes. Different antibody classes are expressed in other species, such like the IgY in birds and reptiles, and IgW in sharks and skates. The reporter gene can also be inserted before the stop codon of the constant region gene of these antibodies too.

As a result of the genetic modification as shown in FIG. 2, the transgenic animals will produce fusion proteins with the reporter protein tagged to the N or C terminal of the antibody heavy chain, as shown in the FIG. 1I and FIG. 1II. Shown in FIG. 1 is a monomer IgG as an example. Other classes of antibodies may form different complexes, such like the IgA dimer and IgM pentamer. The fusion protein may form different complexes according to the antibody class. In all cases the fusion protein should retain the antigen binding capability and able to generate signal from the reporter protein.

Figure 3:
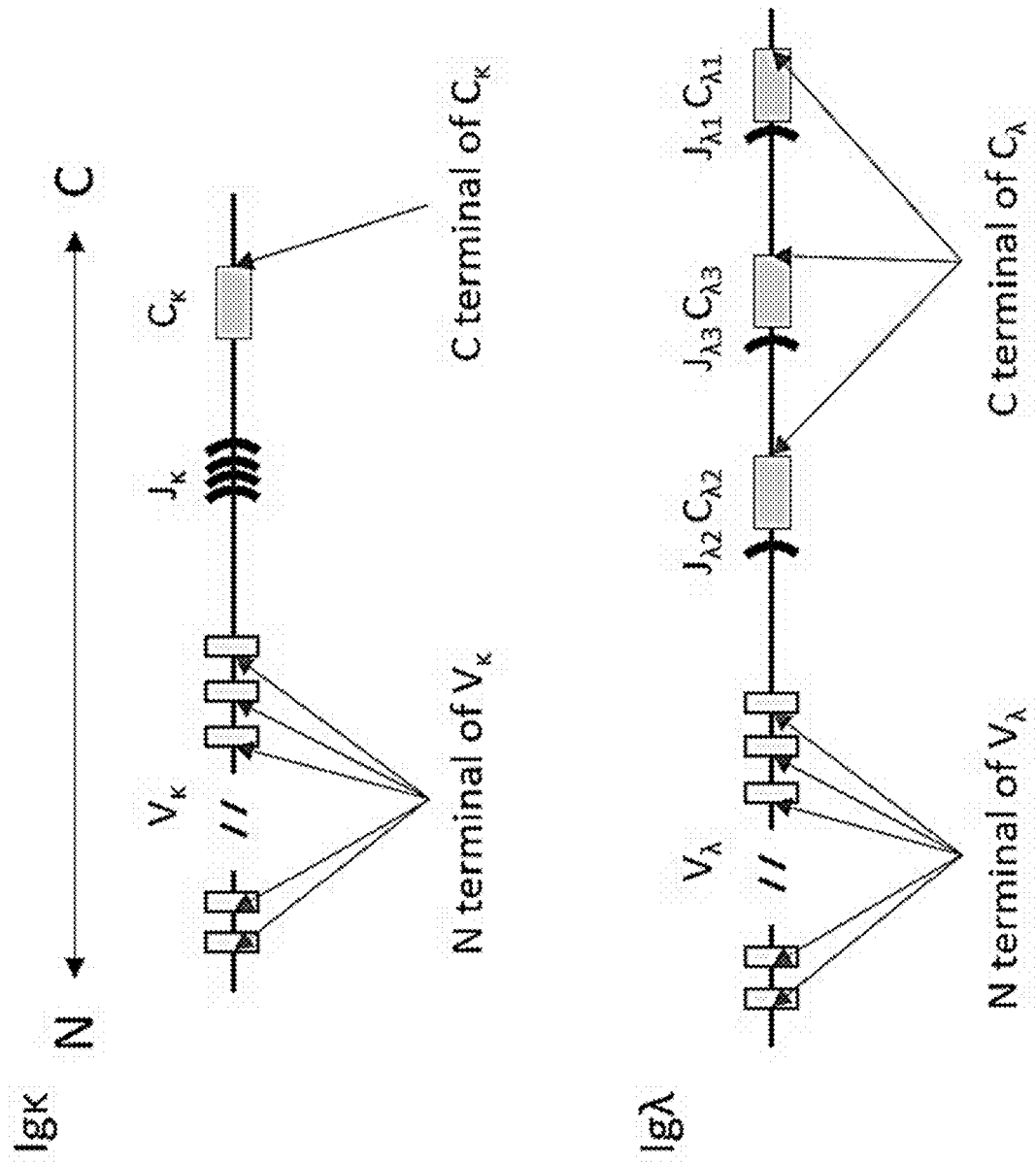
FIG. 3 is a schematic diagram showing exemplary gene fusion sites on the immunoglobulin light chain genes (Igκ or Igλ).

FIG. 3 illustrates the method to fuse the reporter protein gene to the antibody light chains including the κ chain (Igκ) and λ chain (Igλ). The reporter protein gene can be inserted at the N terminal of the V gene of the light chain (Vκ or Vλ), following the ATG start codon. Animals may contain various numbers of Vκ or Vλ genes depending on the species and strains. The reporter gene can be inserted following the ATG start codon of any one of, or any combination of these genes. The reporter protein gene can also be inserted at the C terminal of the constant gene of the light chain (Cκ or Cλ), before the stop codon. Depending on the species animals may contain different numbers of Cκ or Cλ genes, the reporter gene can be inserted before the stop codon of any one of, or any combination of these genes.

As a result of the genetic modification as shown in FIG. 3, the transgenic animals will produce fusion proteins with the reporter protein tagged to the N or C terminal of the antibody light chain, as shown in the FIG. 1III and FIG. 1IV. Other classes of antibodies may form different complexes, such like the IgA dimer and IgM pentamer. The fusion protein may form different complexes according to the antibody class. In all cases the fusion protein should retain the antigen binding capability and able to generate signal from the reporter protein.

Among the above gene targeting loci, the C terminus of the constant region of antibody light chain can include either Igκ or Igλ has been tested and confirmed to produce high quality reporter protein fusion antibodies. Fusion of the reporter protein at the N terminus of the antibody heavy or light chain may interfere with its antigen binding capacity. Fusion of the reporter protein at the C terminus of the antibody heavy chain may interfere with the downstream signaling mediated by the antibody Fc, therefore affect B cell development and antibody production in the animal. Fusion at the C terminus of the antibody light chain is the least likely to cause the above problems, as demonstrated by the in vitro and in vivo test that is disclosed below.

Figure 4:
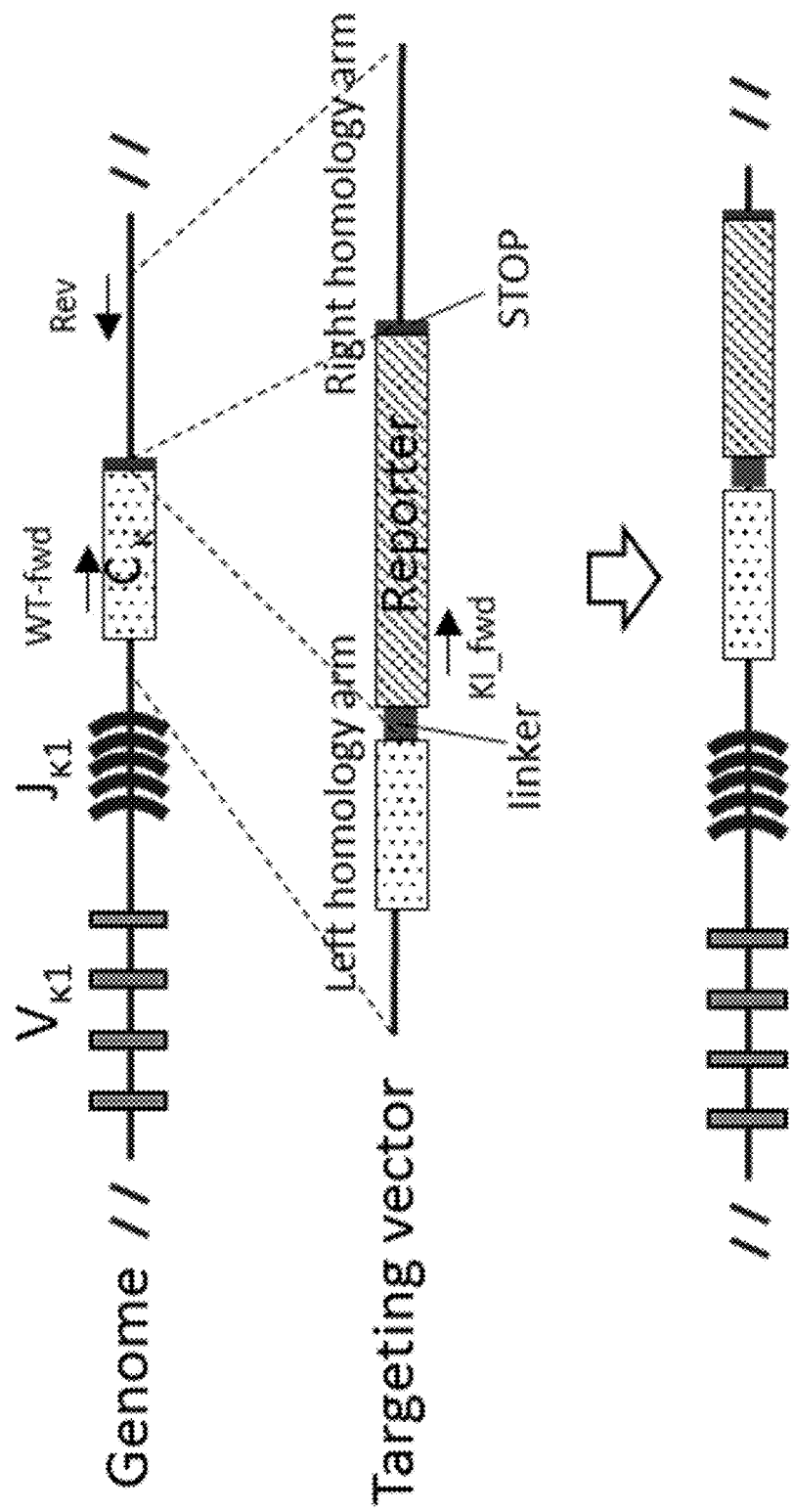
FIG. 4 is a schematic diagram showing an exemplary method of gene targeting to produce the transgenic animals with a reporter gene knocked-in at the C end of antibody κ light chain.

Knock-in of the reporter protein DNA can be achieved by homologous recombination. Programmable nuclease technologies, including zinc finger nucleases (ZFNs), transcription activator-like effector nucleases (TALENs) and CRISPR-Cas9 can be used to facilitate the gene targeting. In all cases a targeting vector is used which consists of a reporter protein DNA with a short linker at the 5' end, flanked by a left homology arm and a right homology arm, as shown in FIG. 4. While the lengths of the left and right homology arms can vary from 100 bp to 100,000 bp, the 3' end of the left arm is located precisely at the end of the antibody light chain (κ or λ) constant region gene with the stop codon removed. The targeting vector can be delivered by either microinjection into the pronuclei of a fertilized egg, or transfection into embryonic stem cells. The fertilized egg or embryonic stem cell injected blastocyst is then implanted into the oviduct of a pseudopregnant surrogate mother to produce the knock-in transgenic animals.

Transgenic animals produced by the gene targeting strategy can be genotyped to confirm the integration of the reporter gene at the right locus, by PCR using the primers illustrated in FIG. 4, or by southern blotting with appropriate restriction enzyme digestion and probes. FIG. 5A shows an example of genotyping the transgenic mice with a luciferase gene knocked-in at the C end of antibody κ gene. Founders (mosaic animals) and homozygous animals are genotyped by PCR, heterozygous animals are genotyped by southern blot. FIG. 5B shows an example of genotyping the transgenic rabbits with a luciferase gene knocked-in at the C end of antibody κ1 gene. Founders (mosaic animals) are genotyped by PCR.

Figure 6B:
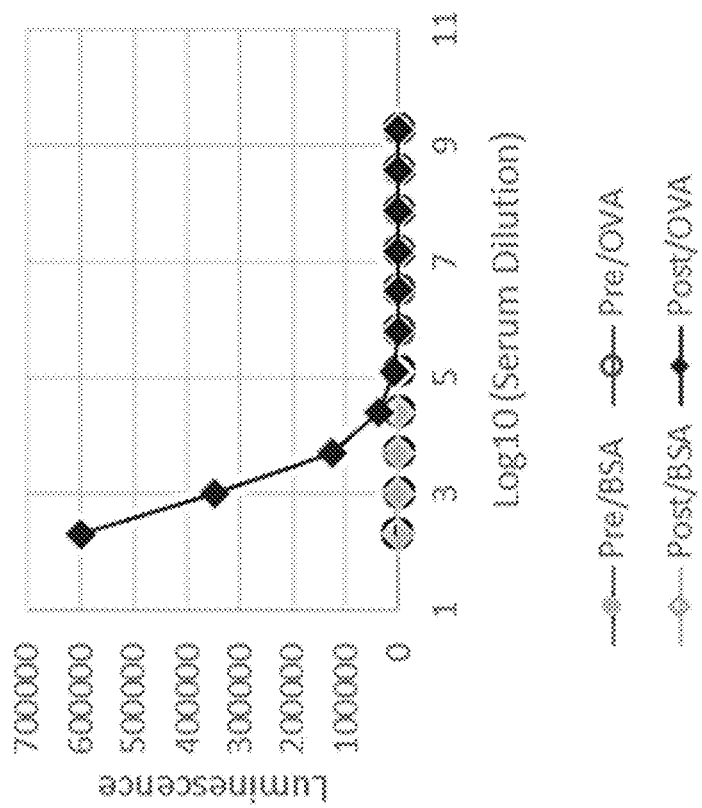
FIG. 6A and FIG. 6B show immunization and production of reporter enzyme fusion antibody from the transgenic animal of the invention.
Figure 6A:
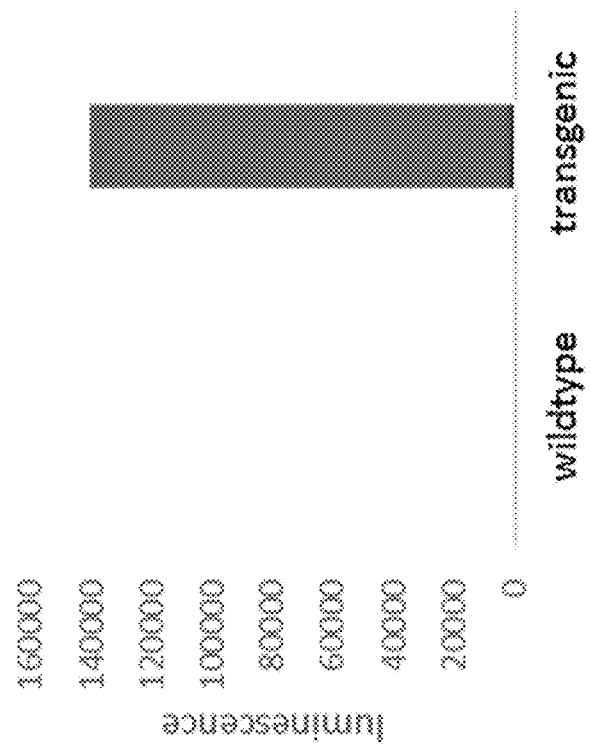

FIG. 6 shows the test and immunization of the transgenic animals of the invention. FIG. 6A shows that a heterozygous animal already produces antibodies with high enzymatic activity in the serum. When substrate is added strong signal is detected which is absent from the wildtype animal serum. In FIG. 6B the transgenic animal is immunized with a specific antigen chicken ovalbumin (OVA). Antibodies specifically recognizing OVA are produced in the transgenic animal post immunization, but absent from the pre immunization animals. Antibodies produced after immunization are specific to OVA, and do not recognize an unrelated protein bovine serum albumin (BSA).

In some implementations, the reporter can be fused as a complete functional protein to the antibody. The fusion protein is immobilized through binding to the antigen, to allow the separation from the unbound proteins in a heterogenous immunoassay. The immobilized complete function reporter protein generates signal to achieve the detection and quantification of the antigen binding. The reporter protein may generate signal upon excitation by a physical signal such as the light, as shown in the left image of FIG. 7. Examples of such reporter protein include, but not limited to green fluorescence protein (GFP) and its variants. The reporter protein may also be an enzyme that generates signal when supplied with its substrate, as shown in the right image of FIG. 7. Examples of such enzymes include, but not limited to horseradish peroxidase (HRP), alkaline phosphatase (AP), luciferase and its variants, β-galactosidase, chloramphenicol acetyl transferase, glucose oxidase, acetate kinase, xanthine oxidase and glucose 6-phosphate dehydrogenase.

Figure 7:
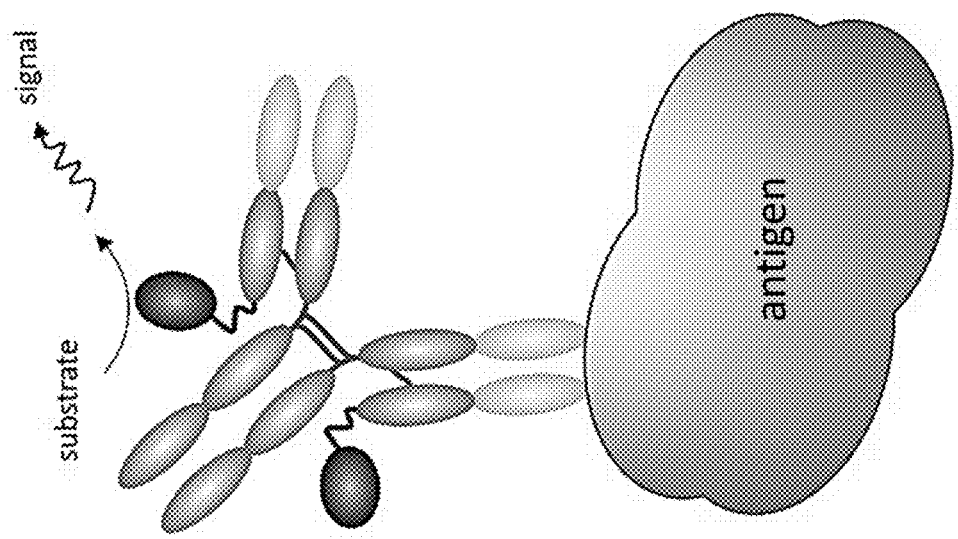
FIG. 7 is a schematic diagram showing an antibody fused with a complete reporter protein, that can bind to an antigen and generate signal upon light excitation (left) or adding substrate (right).
Figure 7:
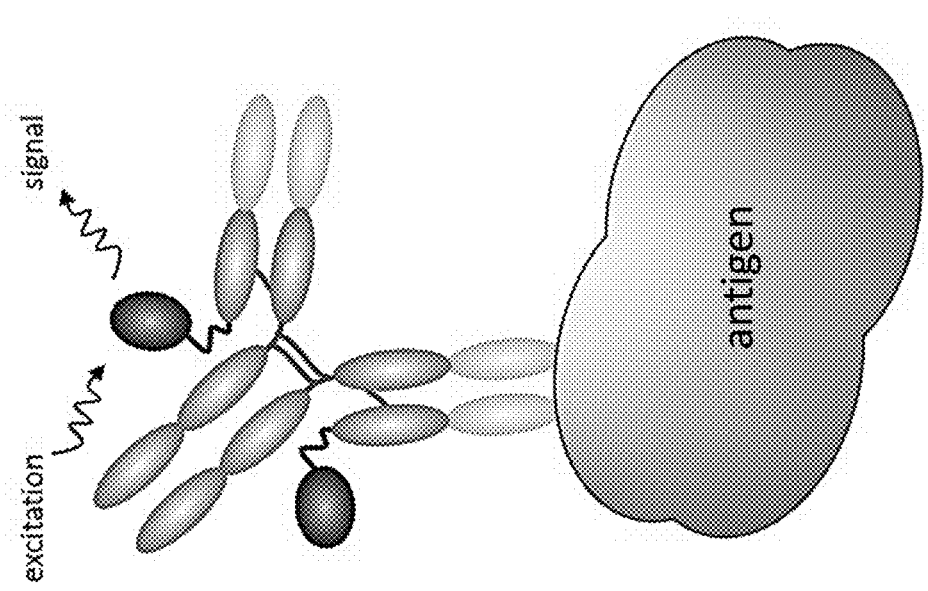
Figure 8:
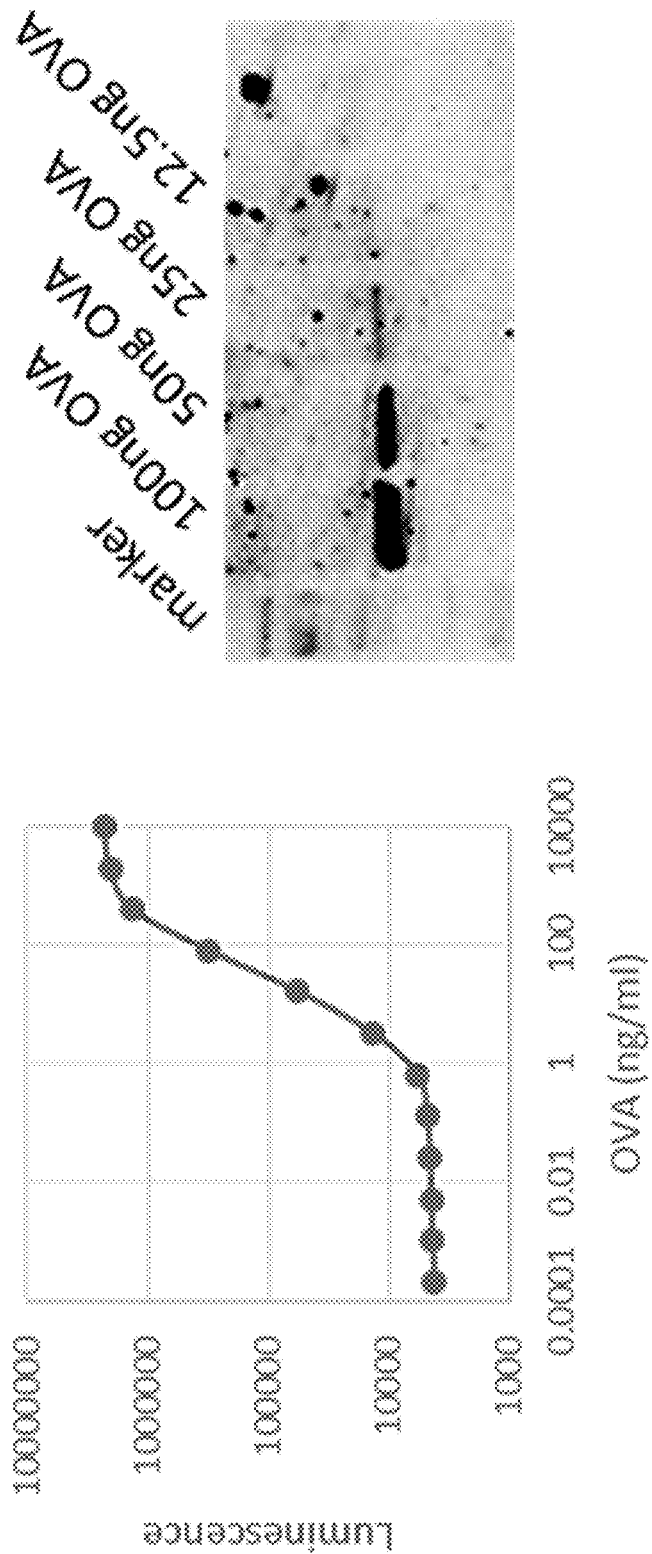
FIG. 8 shows an example of using the reporter enzyme fusion antibody in detecting and measuring the concentration of antigen in ELISA (left) and western blot (right).

FIG. 8 shows an example of using the reporter protein fusion enzyme in immunoassays as illustrated in FIG. 7. The OVA antibody produced from the transgenic animals of the invention are used in ELISA and western blot assay to detect the presence, and measure the concentration of the antigen OVA.

Figure 15B:
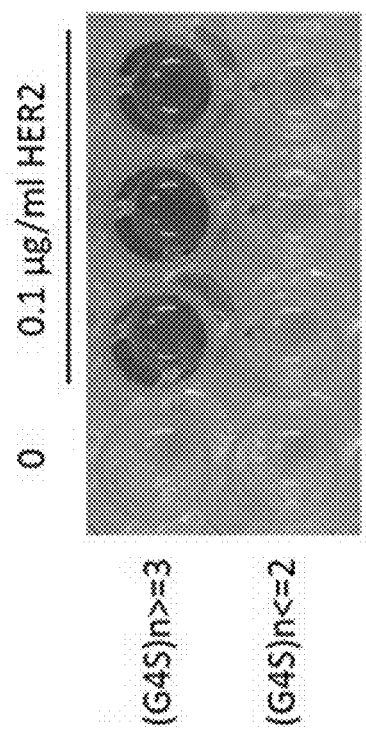
FIG. 15A through FIG. 15C depict experimental results demonstrating the in vitro validation of a horseradish peroxidase (HRP) fused anti-HER2 antibody.
Figure 15C:
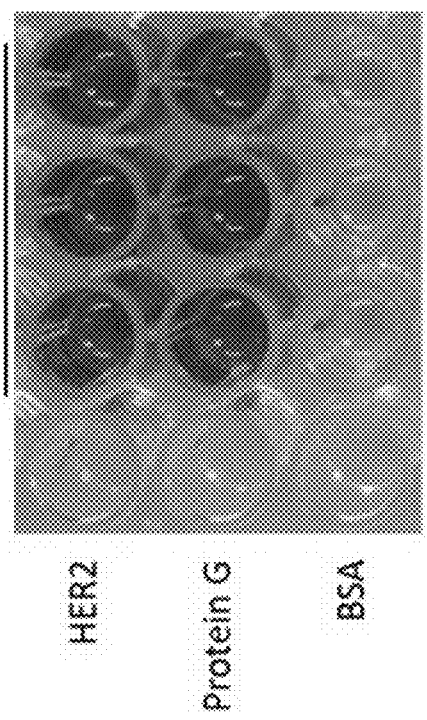
Figure 15A:
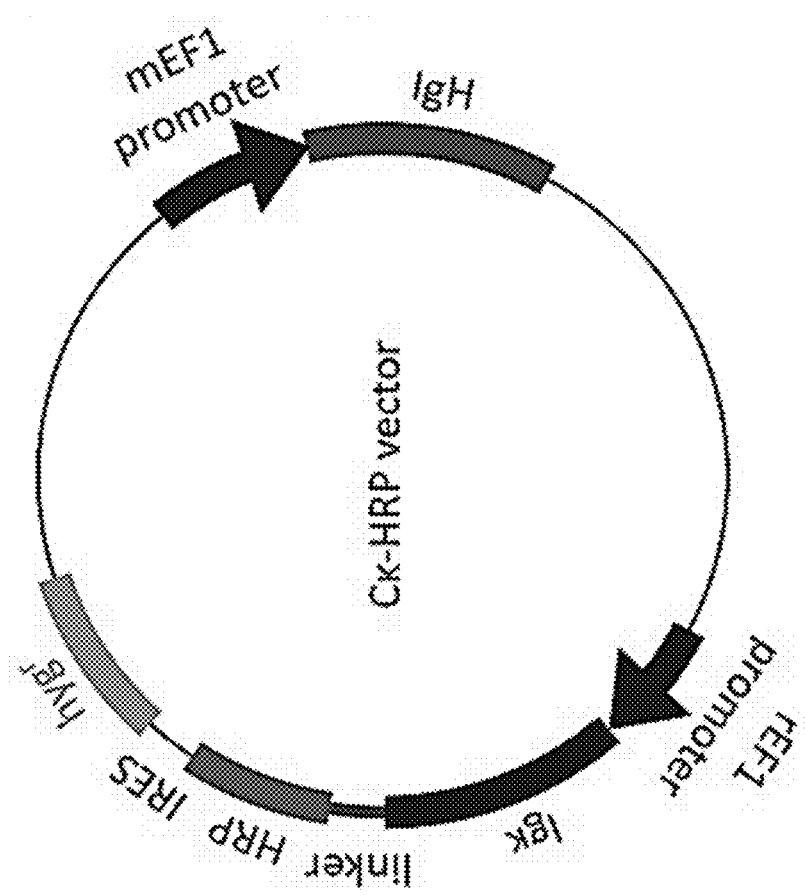

In some implementations the reporter protein, the linker, and the fusion sites of the antibody is tested and validated in vitro before generating the transgenic animal. FIG. 15 shows the in vitro test of a HRP protein fused to an anti-HER2 antibody. In FIG. 15A a mammalian expression vector containing dual promoters were constructed, to drive the expression of the antibody heavy chain and light chain respectively. A DNA sequence encoding a linker and HRP was inserted before the stop codon of the Igκ. Various length of GGGGS (SEQ ID NO:9) repeating peptide ((G4S)n) were tested. FIG. 15B shows that when the linker was longer than or equal to 3 repeats of GGGGS (SEQ ID NO:9) ((G4S)n≥3), the fusion protein produced by transfecting the vector in HEK293 cells retains the binding capability to the immobilized HER2 protein. And the fusion protein retains the HRP enzymatic activity therefore is able to generate colorimetric signal when supplied with the substrate. When the linker length is shorter than 3 repeats of GGGGS (SEQ ID NO:9) ((G4S)n≤2), either the antibody or HRP cannot be folded correctly so that no signal is detected. FIG. 15C shows that the fusion protein with longer than or equal to 3 repeats of GGGGS (SEQ ID NO:9) ((G4S)n≥3) linker retains the protein G binding capacity, that can be used for the protein purification. The specificity of the antibody is also retained and no affinity is detected to the immobilized BSA.

Figure 16B:
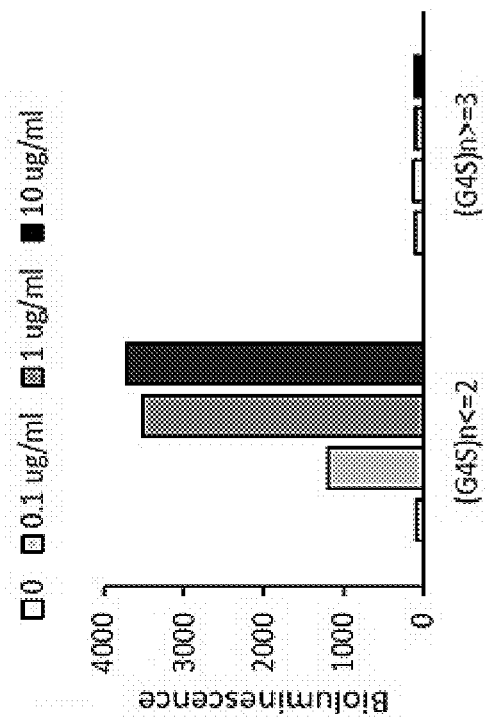
Figure 16B:
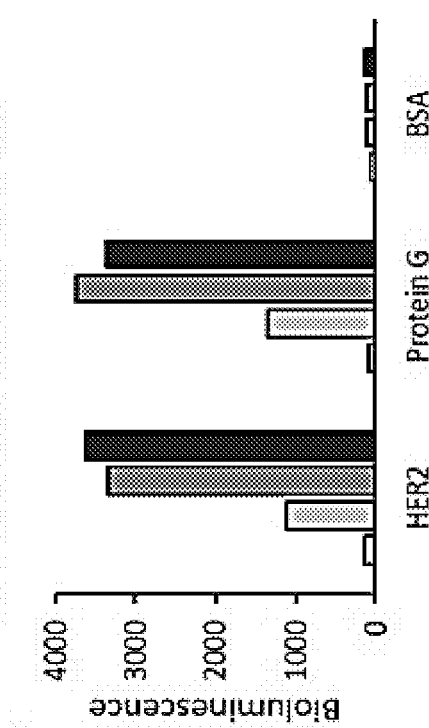
Figure 16A:
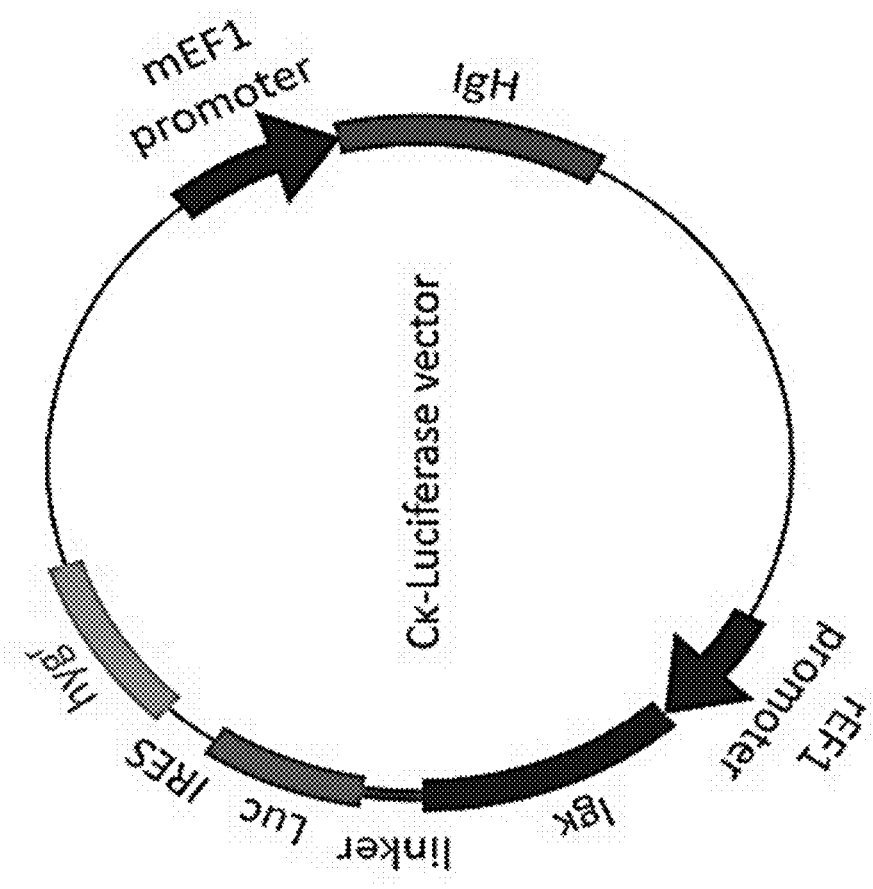

FIG. 16 shows the in vitro test of a luciferase protein fused to an anti-HER2 antibody. In FIG. 16A a mammalian expression vector containing dual promoters were constructed, to drive the expression of the antibody heavy chain and light chain respectively. A DNA sequence encoding a linker and luciferase was inserted before the stop codon of the Igκ. Various length of GGGGS (SEQ ID NO:9) repeating peptide ((G4S)n) were tested. FIG. 16B shows that when the linker was shorter than or equal to 2 repeats of GGGGS (SEQ ID NO:9) ((G4S)n≥2), the fusion protein produced by transfecting the vector in HEK293 cells retains the binding capability to the immobilized HER2 protein. And the fusion protein retains the luciferase enzymatic activity therefore is able to generate bioluminescent signal when supplied with the substrate. When the linker length is longer than 2 repeats of GGGGS (SEQ ID NO:9) ((G4S)n≥3), either the antibody or luciferase cannot be folded correctly so that no signal is detected. FIG. 16C shows that the fusion protein with shorter than or equal to 2 repeats of GGGGS (SEQ ID NO:9) ((G4S)n≤3) linker retains the protein G binding capacity, that can be used for the protein purification. The specificity of the antibody is also retained and no affinity is detected to the immobilized BSA.

Example 2: Proximity Immunoassay Using Reporter Protein Fused Antibodies

This document provides a proximity immunoassay method that uses reporter protein fused antibodies to detect the presence, and/or measure the concentration of an antigen analyte. The immunoassay uses a pair of antibodies of which at least one is fused with a reporter protein. The two antibodies bind to different epitopes on the same antigen molecule, and are brought to close proximity through the binding. Signals are generated as a result of the close proximity through resonance energy transfer to protein fragment complementation mechanism.

This document also provides the method for screening such reporter protein fused antibodies that can be used in the proximity immunoassay. The method involves the use of a transgenic animal producing reporter protein fused antibodies. A two-step procedure, including validation of the screening probe using polyclonal antibodies from the transgenic animal, and screening of the reporter protein fused antibody using monoclonal antibody expression hybridoma or cultured cell clones, is provided. The methods and materials related to an immunoassay using a pair of antibodies recognizing two different epitopes in close proximity on the same antigen are now described.

Proximity Assay

One of, or both antibodies are fused with a reporter protein to serve as the donor or acceptor to generate the immunoassay signal.

In some implementations, the reporter is fused as a complete functional protein to the antibody, and is brought to proximity with another signal generating molecule through binding to the antigen in a homogenous immunoassay. The antigen detection and quantification are measured by the resonance energy transfer between the reporter protein and the proximate molecule. Examples of such implementation include, but not limited to fluorescence resonance energy transfer (FRET) as shown in the left image of FIG. 9, and bioluminescence resonance energy transfer (BRET) as shown in the right image of FIG. 9.

Figure 10:
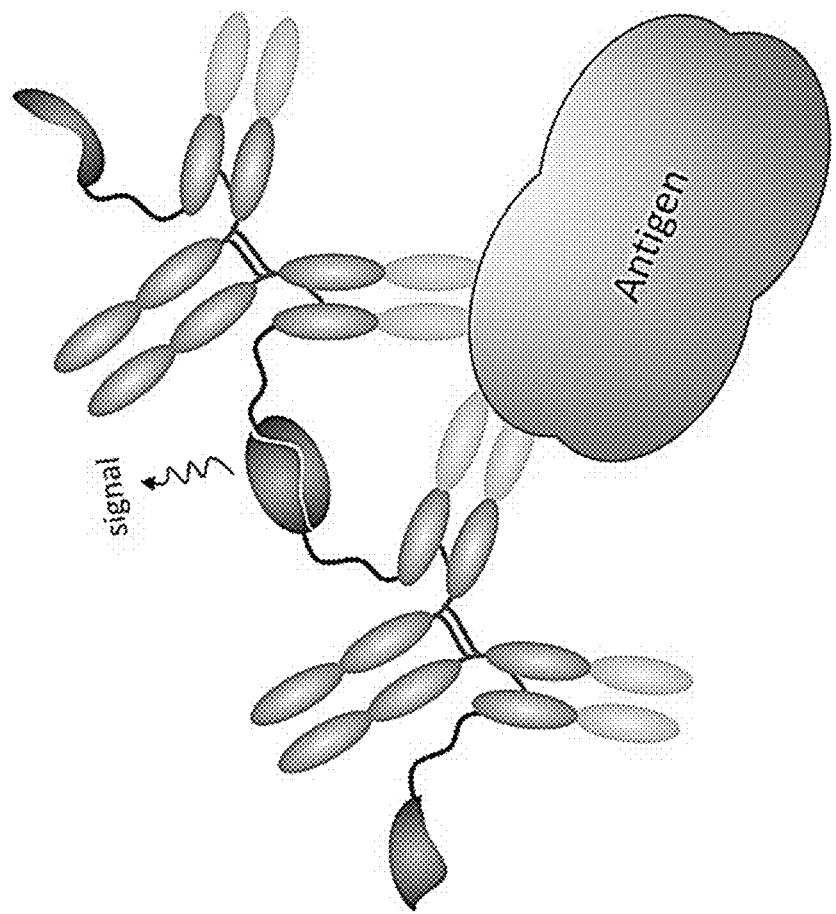
FIG. 10 is a schematic diagram showing a proximity immunoassay using protein-fragment complementation assay (PCA) generated from a pair of reporter protein fused antibodies.

In some implementations, the reporter is fused as a protein fragment to the antibody, and is brought to proximity with the complementary protein fragment through binding to the antigen in a homogenous assay as shown in FIG. 10.

Figure 9:
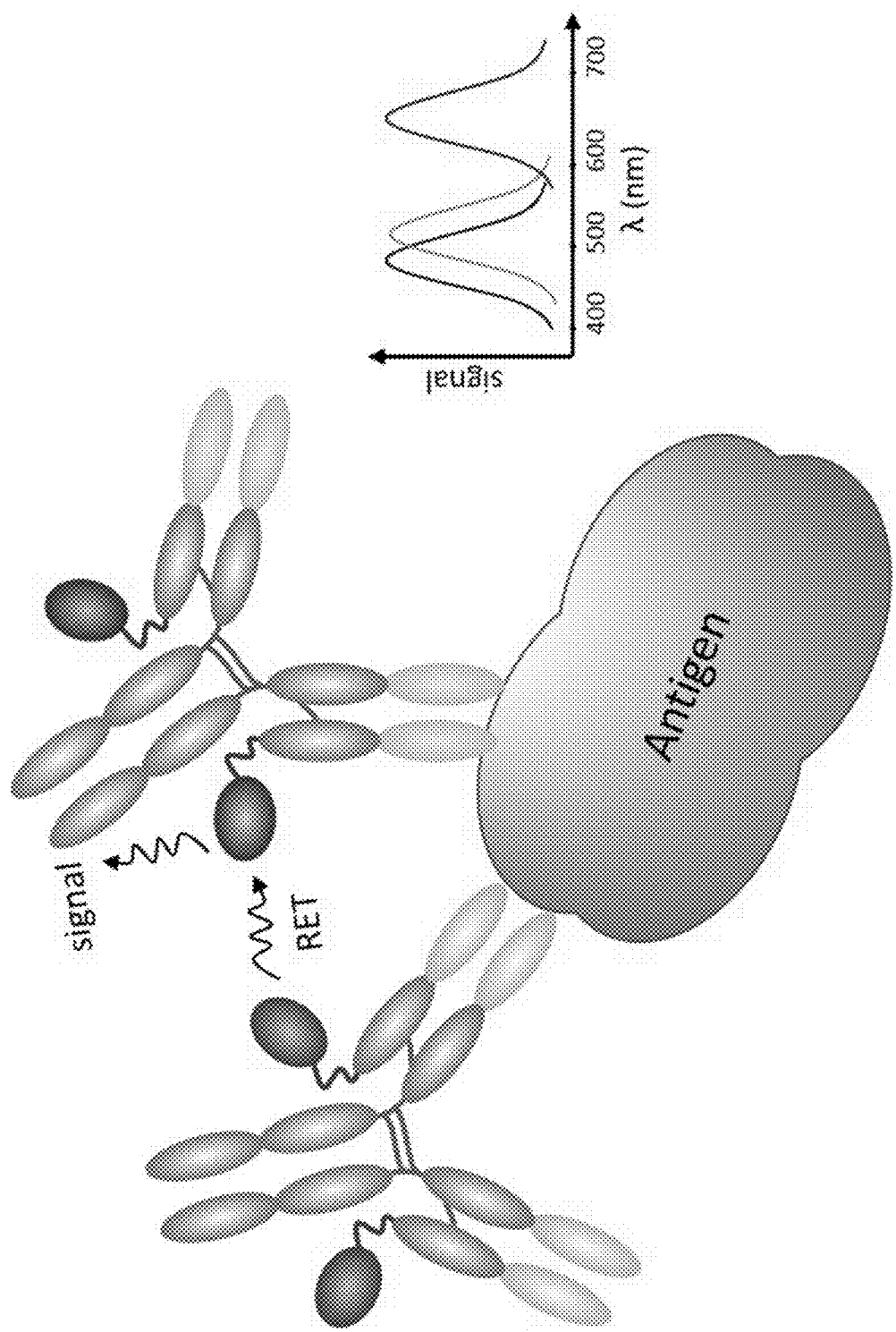
FIG. 9 is a schematic diagram showing a proximity immunoassay using resonance energy transfer (RET) generated from a pair of reporter protein fused antibodies.

In some implementations, two reporter protein fused antibodies are used for antigen detection and quantification. When brought to close proximity through binding to their epitopes on the same antigen, RET occurs between the two reporter genes to generate the antigen specific signal as shown in FIG. 9. The RET can be FRET in which the donor molecule is excited by an excitation light, to activate the donor molecule and generate the signal. The RET can also be BRET in which the donor molecule is provided with a substrate, to generate bioluminescence to activate the donor molecule and generate the signal.

In other implementations, the reaction also utilizes RET mechanism but only one antibody is fused with a reporter protein, while the other antibody is chemically conjugated with a fluorophore to serve as the RET donor or acceptor with the fused reporter protein. In any case at least one reporter protein fused antibody is used, and the emission wavelength of the fluorescence or bioluminescence of the donor molecule overlaps with the excitation wavelength of the acceptor molecule.

In other implementations, two reporter protein fragment fused antibodies are used for antigen detection and quantification. When brought to close proximity through binding to their epitopes on the same antigen, protein fragment complementation occurs to restore the protein activity that can be measured by PCA as shown in FIG. 10.

In other implementations, the reaction also utilizes PCA mechanism but only one antibody is fused with a reporter protein fragment, while the other antibody is chemically conjugated with a complementary protein fragment to serve as the PCA donor or acceptor. In any case at least one reporter protein fused antibody is used.

Figure 11:
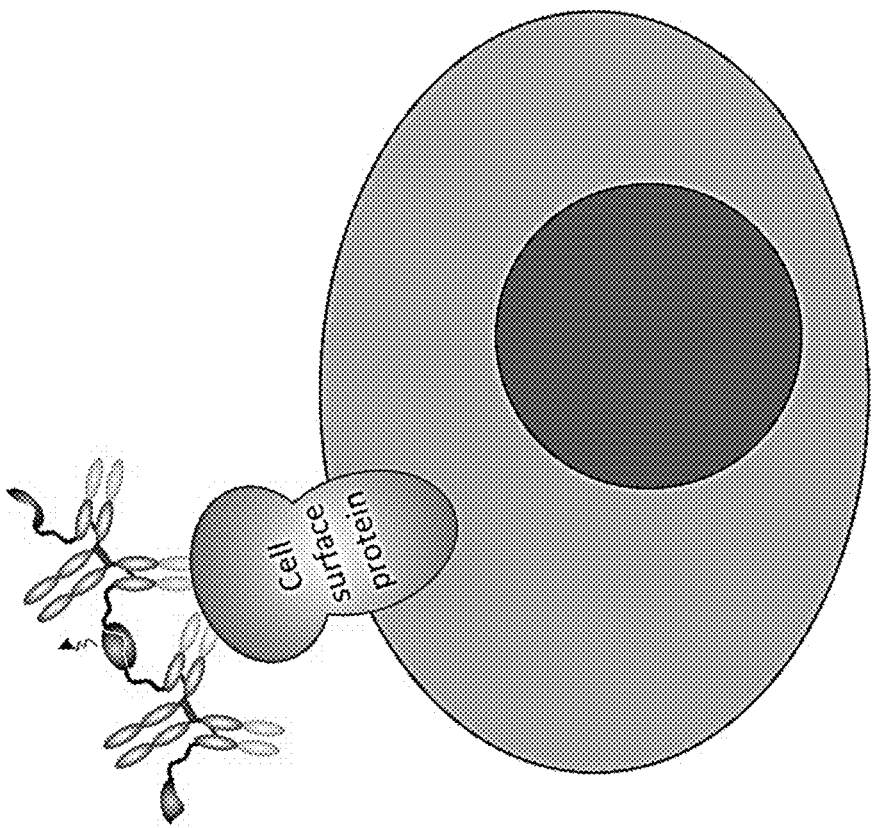
FIG. 11 is a schematic diagram showing the application of the proximity immunoassay in measuring cell membrane protein antigens.
Figure 11:
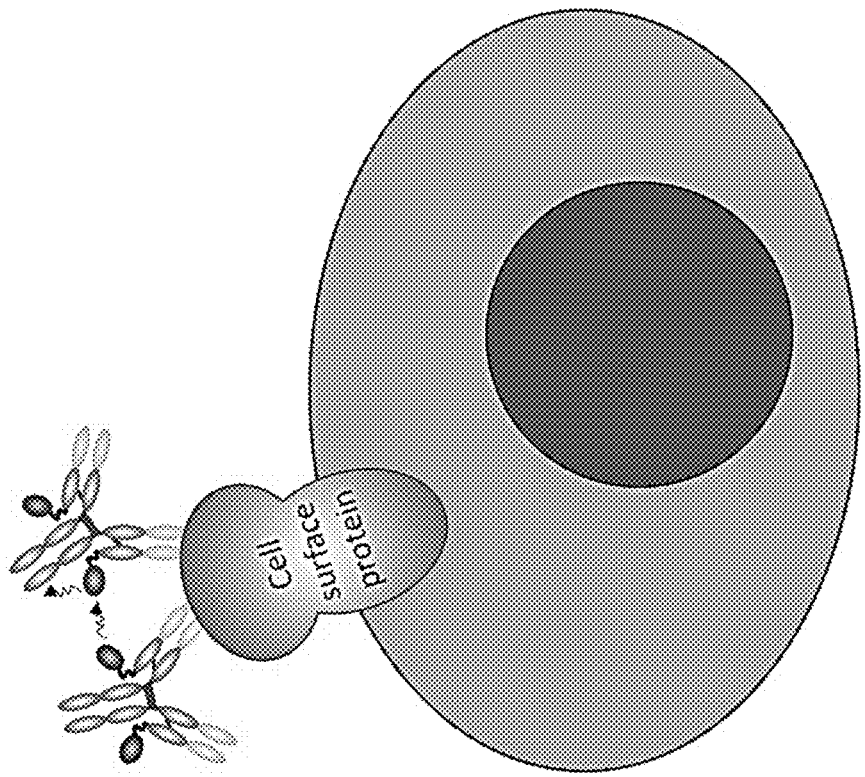

In some implementations, the proximity immunoassay is used for the detection and quantification of cell membrane proteins. The immunoassay can use either the RET mechanism as shown in the left of FIG. 11, or use the PCA mechanism as shown in the right picture of FIG. 11.

Figure 13:
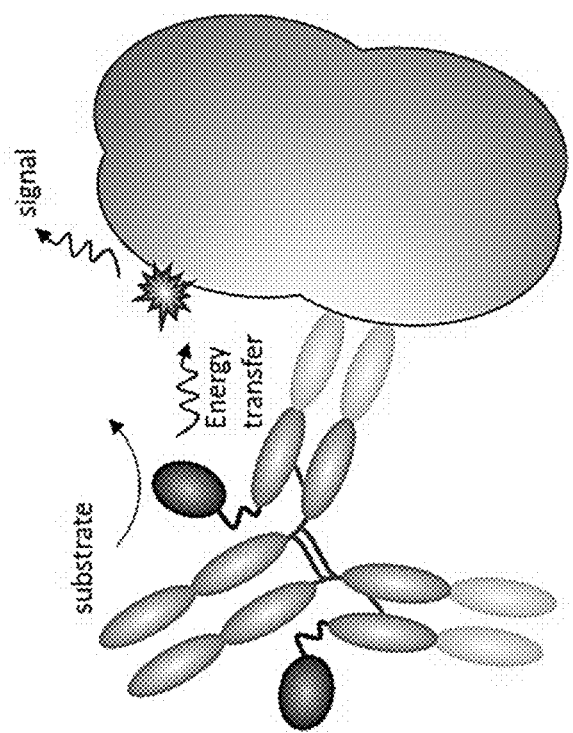
FIG. 13 is a schematic diagram showing an antibody fused with a complete reporter protein, that can generate resonance energy transfer signal with a proximate molecule upon light excitation (left) or adding substrate (right).
Figure 13:
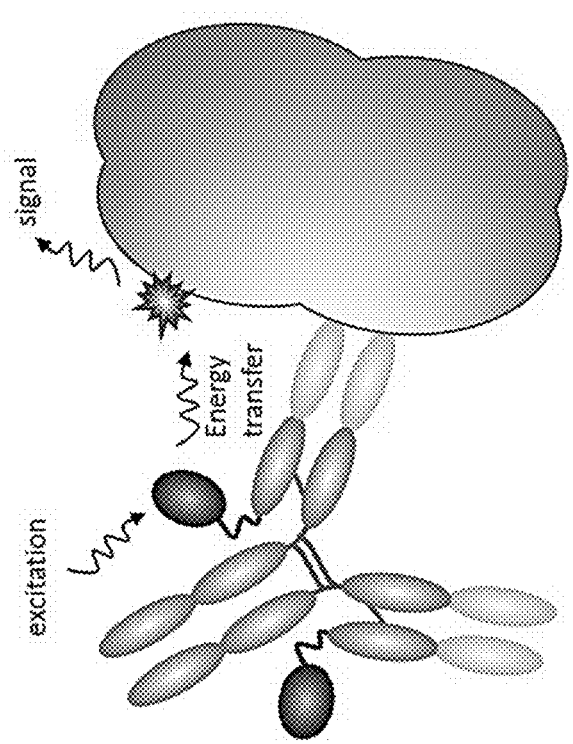

In some implementations, the reaction utilizes RET mechanism but only one antibody is fused with a reporter protein, while the target molecule is chemically conjugated with a fluorophore or is fused with a fluorophore protein to serve as the RET donor or acceptor with the fused reporter protein, as shown in FIG. 13. In any case at least one reporter protein fused antibody is used, and the emission wavelength of the fluorescence or bioluminescence of the donor molecule overlaps with the excitation wavelength of the acceptor molecule.

Figure 14:
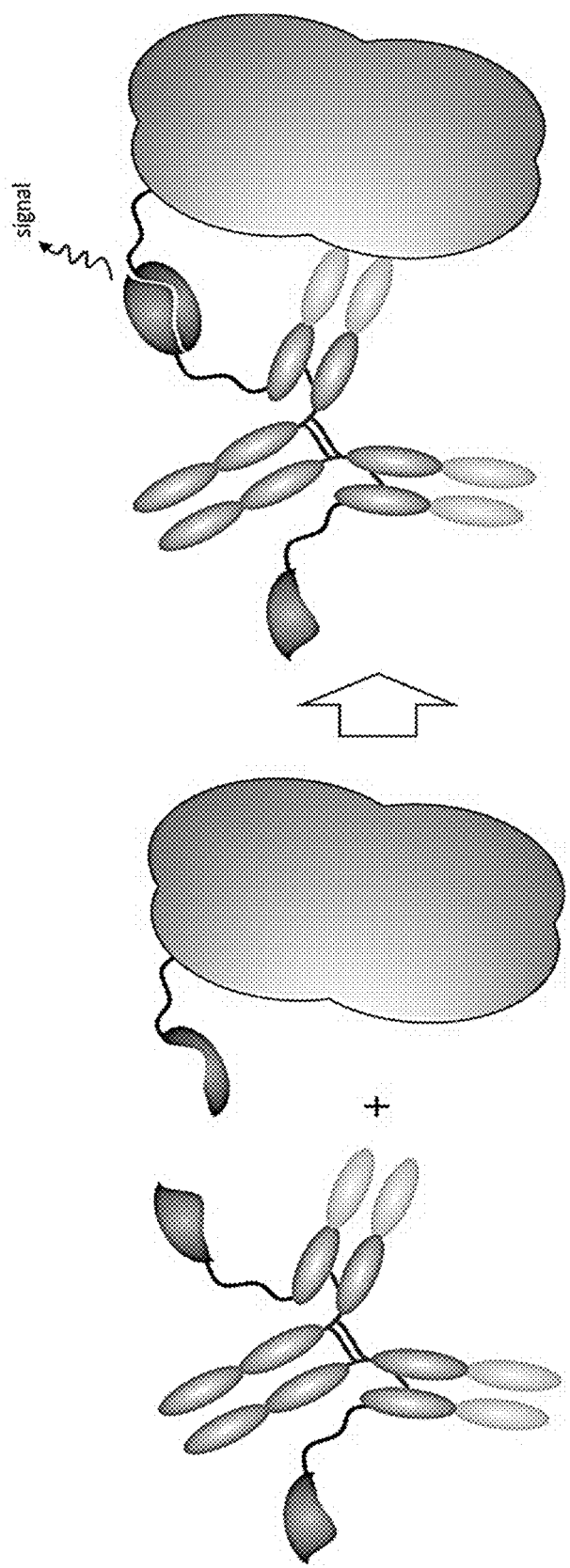
FIG. 14 is a schematic diagram showing an antibody fused with a fragment of reporter protein, that can generate signal upon approaching a complementary fragment of the reporter protein.

In other implementations, the reaction also utilizes PCA mechanism but only one antibody is fused with a reporter protein fragment, while the target molecule is chemically conjugated with or is fused with a complementary protein fragment to serve as the PCA donor or acceptor, as shown in FIG. 14. In any case at least one reporter protein fused antibody is used.

Screening of Reporter Protein Fused Antibodies

Figure 12:
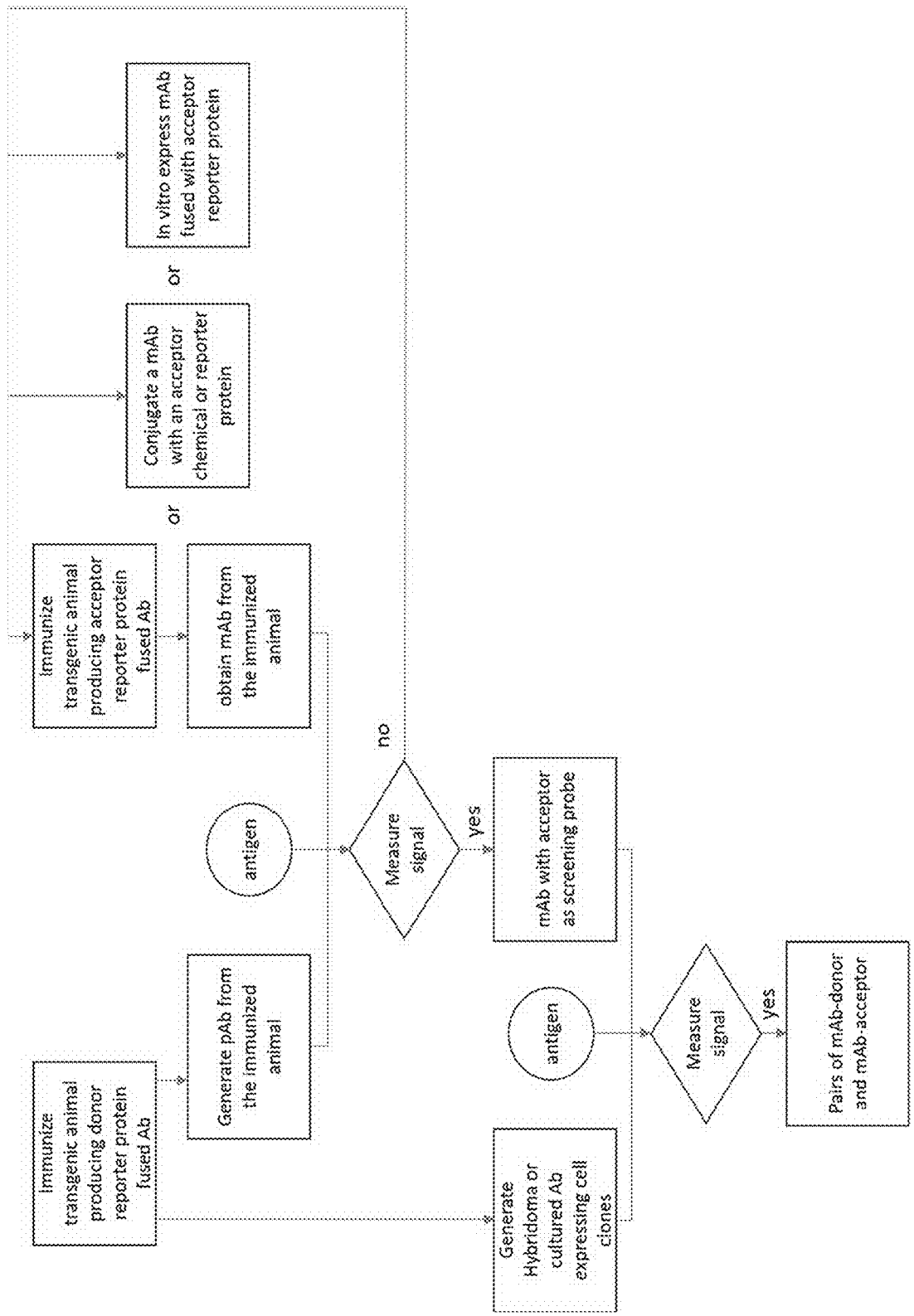
FIG. 12 is a schematic diagram showing a method for screening the proximity immunoassay antibody pairs using transgenic animals producing reporter protein fused antibodies.

FIG. 12 shows a flowchart of an example of a screening method using reporter protein fused antibodies. A first antibody is fused with a donor reporter protein and produced from a transgenic animal. A second antibody is either also produced from a transgenic animal and fused with an acceptor reporter protein; or produced as a traditional mAb and chemically conjugated with an acceptor molecule; or in vitro expressed in cells as an acceptor reporter protein fused antibody.

The second antibody with an acceptor molecule is used as the screening probe. In some implementations, the probe can first be validated by reaction with the antigen, and the donor reporter protein fused pAb generated from the immunized transgenic animals. In other implementation this validation step can be skipped. RET or PCA signals are measured and the acceptor antibody generating strong signals are used as the screening probe.

mAb expressing cells, either hybridoma or cultured cells, are collected to generate a library. Supernatants containing donor reporter protein fused mAbs are collected, then incubated with the antigen and the screening probe to measure the RET or PCA signal. Pairs of mAb donor and acceptor are established from screening the clones generating strong signals.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting at least two target molecules in close proximity in a sample comprising the steps of:
    a) contacting a first target molecule with a first reporter protein fusion antibody derived from a transgenic animal comprising a genomic knock-in modification comprising a nucleotide sequence encoding a reporter protein operably linked to a nucleotide sequence encoding one or more immunoglobulin genes, wherein the knock-in is located at a position selected from the group consisting of the 5' end of a native antibody variable (V) heavy chain gene following the start codon and at the 3' end of a native antibody constant (C) heavy chain gene prior to the stop codon, wherein the first reporter protein fusion antibody comprises an antigen-binding domain linked to the reporter protein or fragment thereof, wherein the antigen binding domain is specific for binding to an epitope on the first target molecule, and wherein the reporter protein of the first reporter protein fusion antibody is selected from the group consisting of a RET donor molecule and a PCA bait protein,
    b) contacting a second target molecule with a second antibody linked to a reporter protein or fragment thereof selected from the group consisting of a RET acceptor molecule and a PCA prey protein, wherein the second antibody comprises an antigen-binding domain specific for binding to an epitope on the second target molecule, and
    c) detecting a detectable signal generated when the first reporter protein fusion antibody is in close proximity to the second antibody.

2. The method of claim 1, wherein the second antibody comprises a second reporter protein fusion antibody derived from a transgenic animal comprising a genomic knock-in modification comprising a nucleotide sequence encoding a reporter protein operably linked to a nucleotide sequence encoding one or more immunoglobulin genes, wherein the knock-in is located at a position selected from the group consisting of the 5' end of a native antibody variable (V) heavy chain gene following the start codon and at the 3' end of a native antibody constant (C) heavy chain gene prior to the stop codon.

* * * * *

SEQUENCE LISTING

```
<160> NUMBER OF SEQ ID NOS: 13

<210> SEQ ID NO 1
<211> LENGTH: 2583
<212> TYPE: DNA
<213> ORGANISM: Artificial Sequence
<220> FEATURE:
<223> OTHER INFORMATION: nucleotide sequence contained in the targeting
      vector to knock-in a HRP gene at the C end of mouse kappa light
      chain

<400> SEQUENCE: 1
ctgtccatac agtaggttta gcttggctac accaaaggaa gccatacaga ggctaatatc      60
agagtattct tggaagagac aggagaaaat gaaagccagt ttctgctctt accttatgtg     120
cttgtgttca gactcccaaa catcaggagt gtcagataaa ctggtctgaa tctctgtctg     180
aagcatggaa ctgaaaagaa tgtagtttca gggaagaaag gcaatagaag gaagcctgag     240
aatatcttca aagggtcaga ctcaatttac tttctaaaga agtagctagg aactagggaa     300
taacttagaa acaacaagat tgtatatatg tgcatcctgg ccccattgtt ccttatctgt     360
agggataagc gtgcttttt gtgtgtctgt atataacata actgtttaca cataatacac     420
tgaaatggag cccttccttg ttacttcata ccatcctctg tgcttccttc ctcagggct      480 gatgctgcac caactgtatc catcttccca ccatccagtg agcagttaac atctggaggt     540
gcctcagtcg tgtgcttctt gaacaacttc taccccaaag acatcaatgt caagtggaag     600
attgatggca gtgaacgaca aaatggcgtc ctgaacagtt ggactgatca ggacagcaaa     660
gacagcacct acagcatgag cagcaccctc acgttgacca aggacgagta tgaacgacat     720
aacagctata cctgtgaggc cactcacaag acatcaactt cacccattgt caagagcttc     780
aacaggaatg agtgtggtgg aggcggttca ggcggaggtg gctctggcgg tggcggatcg     840
atgcagctta ctccaacttt ctacgataac tcttgtccta acgtgagcaa catcgtgcga     900
gatactatcg tgaacgagtt gcggtctgat ccgaggatag ccgcttcaat tttgcggctg     960
catttccacg attgttttgt aaacggctgt gatgcttcca tcctcctcga caataccacc    1020
tctttcagga ctgaaaagga tgccttcggt aacgcgaata gtgctagagg gtttcccgtg    1080
atcgataaga tgaaagccgc tgtggagagc gcctgccccc ggacagttag ttgtgcagac    1140
cttctgacca tagcggccca gcaatccgtg acgctggccg gtgccccag ctggagggtc     1200 cccctgggaa ggagggactc tctgcaggct tttctggact tggcaaacgc aaacctgcct    1260
gctcccttct tcacccttcc ccagctgaag gattccttca ggaatgtcgg cctgaaccga    1320
agtagtgatt tggtggctct gtccggaggc cacacattcg gcaagagtca gtgcaggttc    1380
atcatggaca gactgtataa cttttccaac accggcttgc ctgaccctac cctgaacaca    1440
acatacttgc agactctcag agggctgtgt ccgctcaatg gcaacttgtc tgcactggtt    1500
gactttgacc tgcgcacccc aaccatcttc gacaataagt attacgtcaa tctggaggaa    1560
cagaagggcc tgattcagtc cgaccaggag ctgttcagtt ccccaaatgc taccgacact    1620
attcctcttg tgcgcagctt cgctaatagc acacaaacct ttttcaatgc tttcgtggaa    1680
```

```
gctatggatc ggatgggaaa tataacgccc ctgacgggta cgcagggaca gataagactg    1740
aactgtaggg tcgtgaacag caactctgac ttgaaggacg aactttagag acaaaggtcc    1800
tgagacgcca ccaccagctc cccagctcca tcctatcttc ccttctaagg tcttggaggc    1860
ttcggcacaa gcgacctacc actgttgcgg tgctccaaac ctcctcccca cctccttctc    1920
ctcctcctcc ctttccttgg cttttatcat gctaatattt gcagaaaata ttcaataaag    1980
tgagtctttg cacttgagat ctctgtcttt cttactaaat ggtagtaatc agttgttttt    2040
ccagttacct gggtttctct tctaaagaag ttaaatgttt agttgccctg aaatccacca    2100
cacttaaagg ataaataaaa ccctccactt gccctggttc gctgtccact acatggcagt    2160
cctttctaag gttcacgagt actattcatg gcttattctc tgggccatg gtaggtttga     2220 ggaggcatac ttcctagttt tcttccccta agtcgtcaaa gtcctgaagg gggacagtct    2280
ttacaagcac atgttctgta atctgattca acctacccag taaacttggc gaagcaaagt    2340
agaatcatta tcacaggaag caaaggcaac ctaaatgtgc aagcaatagg aaaatgtgga    2400
agcccatcat agtacttgga cttcatctgc ttttgtgcct tcactaagtt tttaaacatg    2460
agctggctcc tatctgccat tggcaaggct gggcactacc cacaacctac ttcaaggacc    2520
tctataccgt gagattacac acatacatca aaatttggga aaagttctac caagctgaga    2580
gct                                                                  2583
```

<210> SEQ ID NO 2
<211> LENGTH: 2614
<212> TYPE: DNA
<213> ORGANISM: Artificial Sequence
<220> FEATURE:
<223> OTHER INFORMATION: nucleotide sequence contained in the targeting
      vector to knock-in a HRP gene at the C end of rabbit kappa1 light
      chain

<400> SEQUENCE: 2

```
actctgcagg gtgggttggc ctggcctcgc caaggaaggc ccagagagtc ctgatatcac     60
tgcccggtcc tggggagac cagggaaatg aaagccgaga gaggcttccc ttagacgctc     120
gctgcctgct ctgccactgt ccccgtcttc tcctaggaca cagggccggg acctgttcct    180
acttctaaac tccaaagggg tcagatgaaa tgggctgtgt tctttccccg atcactgagt    240
cattgcaggg gcagagtaga gcaacaacaa agaggcctcc cagtgggtca gagagttcac    300
acacaacaac atagactttc tgaaggggca ggcggaaccc ggagggaaac aaagtcatcc    360
agattctacg tctgctcgct gccccattgc aacagctttg gctgcttct gtctgtccat     420 ccctaatgcg ctctgtgatc atccacatgg cacccagggg agatgccac tggtacctaa     480 gccttgccct ctgtgcttct tccctcctca ggtgatccag ttgcacctac tgtcctcatc    540
ttcccaccag ctgctgatca ggtggcaact ggaacagtca ccatcgtgtg tgtggcgaat    600
aaatactttc ccgatgtcac cgtcacctgg gaggtggatg gcaccaccca aacaactggc    660
atcgagaaca gtaaaacacc gcagaattct gcagattgta cctacaacct cagcagcact    720
ctgacactga ccagcacaca gtacaacagc cacaaagagt acacctgcaa ggtgacccag    780
ggcacgacct cagtcgtcca gagcttcaat agggggtgact gtggtggagg cggttcaggc    840
ggaggtggct ctggcggtgg cggatcgatg cagcttactc caactttcta cgataactct    900
tgtcctaacg tgagcaacat cgtgcgagat actatcgtga acgagttgcg gtctgatccg    960
aggatagccg cttcaatttt gcggctgcat ttccacgatt gttttgtaaa cggctgtgat    1020
```

```
gcttccatcc tcctcgacaa taccacctct ttcaggactg aaaaggatgc cttcggtaac    1080
gcgaatagtg ctagagggtt tcccgtgatc gatagaatga aagccgctgt ggagagcgcc    1140
tgcccccgga cagttagttg tgcagacctt ctgaccatag cggcccagca atccgtgacg    1200
ctggccggtg gccccagctg gagggtcccc ctgggaagga gggactctct gcaggctttt    1260
ctggacttgg caaacgcaaa cctgcctgct cccttcttca cccttcccca gctgaaggat    1320
tccttcagga atgtcggcct gaaccgaagt agtgatttgg tggctctgtc cggaggccac    1380
acattcggca agagtcagtg caggttcatc atggacagac tgtataactt ttccaacacc    1440
ggcttgcctg accctaccct gaacacaaca tacttgcaga ctctcagagg gctgtgtccg    1500
ctcaatggca acttgtctgc actggttgac tttgacctgc gcaccccaac catcttcgac    1560
aataagtatt acgtcaatct ggaggaacag aagggcctga ttcagtccga ccaggagctg    1620
ttcagttccc caaatgctac cgacactatt cctcttgtgc gcagcttcgc taatagcaca    1680 caaaccttt tcaatgcttt cgtggaagct atggatcgga tgggaaatat aacgcccctg    1740
acgggtacgc agggacagat aagactgaac tgtagggtcg tgaacagcaa ctctgacttg    1800
aaggacgaac tttaaagcga cgcctgcc agggcaccgc cagtgaccct gaggcccagc    1860
ctcgccgctc cctcccctca gtggacccat tcccaccaca gtcctccagc ccctcccctc    1920
ccggccctca ccccctcctt ggctttaacc ttgcgaatgt tggtgagatg gatgaataaa    1980
gtgaatcttt gcacttgtga cttctctctg cttcttcatt taatggttat tactcatggt    2040
ttcccagttg ccctaaagtc accgccattt catcctccat cccaccctgc cctgctgtcc    2100
tccgggagac accactccct gaaacccaca ggccctgtc ttcacaccgc cgaccccgac    2160
cacacgtgag gggcttgctt cgtgtctcac tcccctcatc gagcccaga gtcctccttt    2220 agtgttctta cagtcacata cagttataca gttcgagtca atccaacctg ccctgccaat    2280
ttcccaaaac aaagattttc agaataaaac agctatgaag aaagtcattt atggaagcat    2340
gatatacaac aacaaaacaa tgcaaacaac ctaactgaat aagcagaggg aaatgttcag    2400
acacactatg gggcttgggc ttcatggagt attacacctt cattcatttt ttaaacttgt    2460
attaaggagc tcctatatta caaggattat actgagcact ttccatgacc taattaattc    2520
tcattacact gtgaggttaa aagcattagt taaaatattg ggcaggctcc ctatagccaa    2580
cagttgttca tattccataa cccaaccatc attt                                2614
```

<210> SEQ ID NO 3
<211> LENGTH: 2133
<212> TYPE: DNA
<213> ORGANISM: Artificial Sequence
<220> FEATURE:
<223> OTHER INFORMATION: nucleotide sequence contained in the targeting
      vector to knock-in a NanoLuc gene at the C end of mouse kappa
      light chain

<400> SEQUENCE: 3

```
ctgtccatac agtaggttta gcttggctac accaaaggaa gccatacaga ggctaatatc      60
agagtattct tggaagagac aggagaaaat gaaagccagt ttctgctctt accttatgtg     120
cttgtgttca gactcccaaa catcaggagt gtcagataaa ctggtctgaa tctctgtctg     180
aagcatggaa ctgaaaagaa tgtagtttca gggaagaaag gcaatagaag gaagcctgag     240
aatatcttca aagggtcaga ctcaatttac tttctaaaga agtagctagg aactagggaa     300
taacttagaa acaacaagat tgtatatatg tgcatcctgg ccccattgtt ccttatctgt     360
agggataagc gtgctttttt gtgtgtctgt atataacata actgtttaca cataatacac     420
```

```
tgaaatggag cccttccttg ttacttcata ccatcctctg tgcttccttc ctcagggct    480 gatgctgcac caactgtatc catcttccca ccatccagtg agcagttaac atctggaggt   540
gcctcagtcg tgtgcttctt gaacaacttc taccccaaag acatcaatgt caagtggaag   600
attgatggca gtgaacgaca aaatggcgtc ctgaacagtt ggactgatca ggacagcaaa   660
gacagcacct acagcatgag cagcaccctc acgttgacca aggacgagta tgaacgacat   720
aacagctata cctgtgaggc cactcacaag acatcaactt cacccattgt caagagcttc   780
aacaggaatg agtgtggtgg aggcggttca ggcggaggtg gctctgtctt cacactcgaa   840
gatttcgttg gggactggcg acagacagcc ggctacaacc tggaccaagt ccttgaacag   900
ggaggtgtgt ccagtttgtt tcagaatctc ggggtgtccg taactccgat ccaaaggatt   960
gtcctgagcg tgaaaatgg gctgaagatc gacatccatg tcatcatccc gtatgaaggt   1020
ctgagcggcg accaaatggg ccagatcgaa aaaatttta aggtggtgta ccctgtggat   1080
gatcatcact ttaaggtgat cctgcactat ggcacactgg taatcgacgg ggttacgccg   1140
aacatgatcg actatttcgg acggccgtat gaaggcatcg ccgtgttcga cggcaaaaag   1200
atcactgtaa cagggaccct gtggaacggc aacaaaatta tcgacgagcg cctgatcaac   1260
cccgacggct ccctgctgtt ccgagtaacc atcaacggag tgaccggctg cggctgtgc    1320 gaacgcattc tggcgtagag acaaaggtcc tgagacgcca ccaccagctc ccagctcca    1380 tcctatcttc ccttctaagg tcttggaggc ttcggcacaa gcgacctacc actgttgcgg   1440
tgctccaaac ctcctcccca cctccttctc ctcctcctcc cttttccttgg cttttatcat   1500 gctaatattt gcagaaaata ttcaataaag tgagtctttg cacttgagat ctctgtcttt   1560
cttactaaat ggtagtaatc agttgttttt ccagttacct gggtttctct tctaaagaag   1620
ttaaatgttt agttgccctg aaatccacca cacttaaagg ataaataaaa ccctccactt   1680
gccctggttc gctgtccact acatggcagt ccttttctaag gttcacgagt actattcatg   1740
gcttatttct ctgggccatg gtaggtttga ggaggcatac ttcctagttt tcttcccta    1800 agtcgtcaaa gtcctgaagg gggacagtct ttacaagcac atgttctgta atctgattca   1860
acctacccag taaacttggc gaagcaaagt agaatcatta tcacaggaag caaaggcaac   1920
ctaaatgtgc aagcaatagg aaaatgtgga agcccatcat agtacttgga cttcatctgc   1980
ttttgtgcct tcactaagtt tttaaacatg agctggctcc tatctgccat ggcaaggct    2040 gggcactacc cacaacctac ttcaaggacc tctataccgt gagattacac acatacatca   2100
aaatttggga aaagttctac caagctgaga gct                                2133
```

<210> SEQ ID NO 4
<211> LENGTH: 2164
<212> TYPE: DNA
<213> ORGANISM: Artificial Sequence
<220> FEATURE:
<223> OTHER INFORMATION: nucleotide sequence contained in the targeting
      vector to knock-in a NanoLuc gene at the C end of rabbit kappa1
      light chain

<400> SEQUENCE: 4

```
actctgcagg gtgggttggc ctggcctcgc caaggaaggc ccagagagtc ctgatatcac    60
tgcccggtcc tgggggagac cagggaaatg aaagccgaga gaggcttccc ttagacgctc   120
gctgcctgct ctgccactgt ccccgtcttc tcctaggaca cagggccggg acctgttcct   180
acttctaaac tccaaagggg tcagatgaaa tgggctgtgt ctttccccg atcactgagt    240
```

```
cattgcaggg gcagagtaga gcaacaacaa agaggcctcc cagtgggtca gagagttcac    300
acacaacaac atagactttc tgaaggggca ggcggaaccc ggagggaaac aaagtcatcc    360
agattctacg tctgctcgct gccccattgc aacagctttg gctgcttct gtctgtccat     420 ccctaatgcg ctctgtgatc atccacatgg cacccagggg agatgcccac tggtacctaa    480
gccttgccct ctgtgcttct tccctcctca ggtgatccag ttgcacctac tgtcctcatc    540
ttcccaccag ctgctgatca ggtggcaact ggaacagtca ccatcgtgtg tgtggcgaat    600
aaatactttc ccgatgtcac cgtcacctgg gaggtggatg gcaccaccca acaactggc     660 atcgagaaca gtaaaacacc gcagaattct gcagattgta cctacaacct cagcagcact    720
ctgacactga ccagcacaca gtacaacagc cacaaagagt acacctgcaa ggtgacccag    780
ggcacgacct cagtcgtcca gagcttcaat aggggtgact gtggtggagg cggttcaggc    840
ggaggtggct ctgtcttcac actcgaagat ttcgttgggg actggcgaca gacagccggc    900
tacaacctgg accaagtcct gaacagggga gtgtgtcca gtttgtttca gaatctcggg     960
gtgtccgtaa ctccgatcca aaggattgtc ctgagcggtg aaaatgggct gaagatcgac    1020
atccatgtca tcatcccgta tgaaggtctg agcggcgacc aaatgggcca gatcgaaaaa    1080 attttaagg tggtgtaccc tgtgatgat catcacttta aggtgatcct gcactatggc     1140
acactggtaa tcgacggggt tacgccgaac atgatcgact atttcggacg gccgtatgaa    1200
ggcatcgccg tgttcgacgg caaaaagatc actgtaacag ggaccctgtg aacggcaac     1260 aaaattatcg acgagcgcct gatcaacccc gacggctccc tgctgttccg agtaaccatc    1320
aacggagtga ccggctggcg gctgtgcgaa cgcattctgg cgtaaagcga gacgcctgcc    1380
agggcaccgc cagtgaccct gaggcccagc ctcgccgctc cctcccctca gtggacccat    1440
tcccaccaca gtcctccagc ccctccctc ccggccctca cccctccctt ggctttaacc      1500
ttgcgaatgt tggtgagatg gatgaataaa gtgaatcttt gcacttgtga cttctctctg    1560
cttcttcatt taatggttat tactcatggt ttcccagttg ccctaaagtc accgccattt    1620
catcctccat cccaccctgc cctgctgtcc tccgggagac accactccct gaaacccaca    1680 ggccctgtc ttcacaccgc cgaccccgac cacgtgag gggcttgctt cgtgtctcac        1740
tcccctcatc gagccccaga gtcctccttt agtgttctta cagtcacata cagttataca    1800
gttcgagtca atccaacctg ccctgccaat ttcccaaaac aaagattttc agaataaaac    1860
agctatgaag aaagtcattt atggaagcat gatatacaac aacaaaacaa tgcaaacaac    1920
ctaactgaat aagcagaggg aaatgttcag acacactatg gggcttgggc ttcatggagt    1980 attaccctt cattacattt ttaaacttgt attaaggagc tcctatatta caaggattat     2040
actgagcact ttccatgacc taattaattc tcattacact gtgaggttaa agcattagt     2100 taaaatattg ggcaggctcc ctatagccaa cagttgttca tattccataa cccaaccatc    2160
attt                                                                 2164
```

<210> SEQ ID NO 5
<211> LENGTH: 441
<212> TYPE: PRT
<213> ORGANISM: Artificial Sequence
<220> FEATURE:
<223> OTHER INFORMATION: amino acid sequence of anti-VEGFA heavy chain
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 5

```
Gln Glu Gln Leu Val Glu Ser Gly Gly Arg Leu Val Thr Pro Gly Thr
1               5                   10                  15

Pro Leu Thr Leu Thr Cys Thr Val Ser Gly Ile Asp Leu Ser Arg Tyr
            20                  25                  30

Gly Met Thr Trp Val Arg Gln Ala Pro Gly Lys Gly Leu Glu Trp Ile
        35                  40                  45

Gly Ile Ile Gly Gly Ser Gly Leu Thr Tyr Tyr Ala Asn Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Arg Gly His Gly Pro Pro Ile Ser Val Val
                85                  90                  95

Glu Asp Thr Ile Val Val Leu Met Leu Xaa Arg Ser Gly Ala Gln Ala
            100                 105                 110

Pro Trp Xaa Thr Val Ser Ser Gln Pro Lys Ala Pro Ser Val Phe Pro
        115                 120                 125

Leu Ala Pro Cys Cys Gly Asp Thr Pro Ser Ser Thr Val Thr Leu Gly
    130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Ser Val Val Ser Val Thr Ser Ser
            180                 185                 190

Ser Gln Pro Val Thr Cys Asn Val Ala His Pro Ala Thr Asn Thr Lys
        195                 200                 205

Val Asp Lys Thr Val Ala Pro Ser Thr Cys Ser Lys Pro Thr Cys Pro
    210                 215                 220

Pro Pro Glu Leu Leu Gly Gly Pro Ser Val Phe Ile Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Asp Asp Pro Glu Val Gln Phe Thr Trp Tyr
            260                 265                 270

Ile Asn Asn Glu Gln Val Arg Thr Ala Arg Pro Pro Leu Arg Glu Gln
        275                 280                 285

Gln Phe Asn Ser Thr Ile Arg Val Val Ser Thr Leu Pro Ile Ala His
    290                 295                 300

Gln Asp Trp Leu Arg Gly Lys Glu Phe Lys Cys Lys Val His Asn Lys
305                 310                 315                 320

Ala Leu Pro Ala Pro Ile Glu Lys Thr Ile Ser Lys Ala Arg Gly Gln
                325                 330                 335

Pro Leu Glu Pro Lys Val Tyr Thr Met Gly Pro Pro Arg Glu Glu Leu
            340                 345                 350

Ser Ser Arg Ser Val Ser Leu Thr Cys Met Ile Asn Gly Phe Tyr Pro
        355                 360                 365

Ser Asp Ile Ser Val Glu Trp Glu Lys Asn Gly Lys Ala Glu Asp Asn
    370                 375                 380

Tyr Lys Thr Thr Pro Ala Val Leu Asp Ser Asp Gly Ser Tyr Phe Leu
385                 390                 395                 400
```

Tyr Ser Lys Leu Ser Val Pro Thr Ser Glu Trp Gln Arg Gly Asp Val
            405                 410                 415

Phe Thr Cys Ser Val Met His Glu Ala Leu His Asn His Tyr Thr Gln
        420                 425                 430

Lys Ser Ile Ser Arg Ser Pro Gly Lys
        435                 440

<210> SEQ ID NO 6
<211> LENGTH: 1323
<212> TYPE: DNA
<213> ORGANISM: Artificial Sequence
<220> FEATURE:
<223> OTHER INFORMATION: nucleotide sequence of anti-VEGFA heavy chain
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t

<400> SEQUENCE: 6
caggagcagc tggtggagtc cggggggtcgc ctggtcacgc tgggacacc cctgacactc      60 acctgcacag tctctggaat cgacctcagt aggtatggaa tgacctgggt ccgccaggct     120
ccagggaagg gctggaatg gatcgggatc attggtggta gtggtctcac atactacgcg     180
aactgggcga aggccgatt caccatctcc aaaacctcgt cgaccacggt ggatctgaag     240
atgaccagtc tgacaacccg aggacacggn ccacctattt ctgttgtaga ggacacgatc     300
gtagtgctta tgcttgntcg atctggggcc caggcaccct ggtncaccgt ctcttcacaa     360
cctaaggctc catcagtctt cccactggcc cctgctgcg ggacacacc cagctccacg      420 gtgaccctgg gctgcctggt caaaggctac ctcccggagc cagtgaccgt gacctggaac     480
tcgggcaccc tcaccaatgg ggtacgcacc ttcccgtccg tccggcagtc ctcaggcctc     540
tactcgctga gcagcgtggt gagcgtgacc tcaagcagcc agcccgtcac ctgcaacgtg     600
gcccacccag ccaccaacac caaagtggac aagaccgttg cgcctcgac atgcagcaag     660 cccacgtgcc caccccctga actcctgggg ggaccgtctg tcttcatctt ccccccaaaa     720
cccaaggaca ccctcatgat ctcacgcacc cccgaggtca catgcgtggt ggtgacgtg     780 agccaggatg accccgaggt gcagttcaca tggtacataa acaacgagca ggtgcgcacc     840
gcccggccgc cgctacggga gcagcagttc aacagcacga tccgcgtggt cagcaccctc     900
cccatcgcgc accaggactg gctgaggggc aaggagttca gtgcaaagt ccacaacaag      960 gcactcccgg cccccatcga gaaaaccatc tccaaagcca gagggcagcc cctggagccg    1020
aaggtctaca ccatgggccc tccccgggag gagctgagca gcaggtcggt cagcctgacc    1080
tgcatgatca acggcttcta cccttccgac atctcggtgg agtgggagaa gaacggaag     1140 gcagaggaca ctacaagac cacgccggcc gtgctggaca cgacggctc ctacttcctc      1200 tacagcaagc tctcagtgcc cacgagtgag tggcagcggg gcgacgtctt cacctgctcc    1260
gtgatgcacg aggccttgca caaccactac acgcagaagt ccatctcccg ctctccgggt    1320
aaa                                                                    1323

<210> SEQ ID NO 7
<211> LENGTH: 541
<212> TYPE: PRT
<213> ORGANISM: Artificial Sequence
<220> FEATURE:
<223> OTHER INFORMATION: amino acid sequence encoding anti-VEGFA light
      chain linked to HRP via a (G4S)3 linker

<400> SEQUENCE: 7

```
Ala Leu Val Met Thr Gln Thr Pro Ser Ser Val Ser Ala Ala Val Gly
1               5                   10                  15

Asp Thr Val Thr Ile Lys Cys Gln Ala Ser Gln Ser Ile Asn Ala Tyr
            20                  25                  30

Leu Ala Trp Tyr Gln Gln Lys Pro Gly Gln Pro Pro Lys Leu Leu Ile
        35                  40                  45

Tyr Gln Ala Ser Asn Leu Ala Ser Gly Val Pro Ser Arg Phe Lys Gly
50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Thr Arg Thr Ala Gly Asp
                85                  90                  95

Val Ala Phe Gly Gly Gly Thr Lys Leu Glu Ile Lys Asp Pro Val Ala
            100                 105                 110

Pro Thr Val Leu Ile Phe Pro Pro Ala Ala Asp Gln Val Ala Thr Gly
        115                 120                 125

Thr Val Thr Ile Val Cys Val Ala Asn Lys Tyr Phe Pro Asp Val Thr
130                 135                 140

Val Thr Trp Glu Val Asp Gly Thr Thr Gln Thr Thr Gly Ile Glu Asn
145                 150                 155                 160

Ser Lys Thr Pro Gln Asn Ser Ala Asp Cys Thr Tyr Asn Leu Ser Ser
                165                 170                 175

Thr Leu Thr Leu Thr Ser Thr Gln Tyr Asn Ser His Lys Glu Tyr Thr
            180                 185                 190

Cys Lys Val Thr Gln Gly Thr Thr Ser Val Val Gln Ser Phe Asn Arg
        195                 200                 205

Gly Asp Cys Gly Gly Gly Gly Ser Gly Gly Gly Gly Ser Gly Gly Gly
210                 215                 220

Gly Ser Met Gln Leu Thr Pro Thr Phe Tyr Asp Asn Ser Cys Pro Asn
225                 230                 235                 240

Val Ser Asn Ile Val Arg Asp Thr Ile Val Asn Glu Leu Arg Ser Asp
                245                 250                 255

Pro Arg Ile Ala Ala Ser Ile Leu Arg Leu His Phe His Asp Cys Phe
            260                 265                 270

Val Asn Gly Cys Asp Ala Ser Ile Leu Leu Asp Asn Thr Thr Ser Phe
        275                 280                 285

Arg Thr Glu Lys Asp Ala Phe Gly Asn Ala Asn Ser Ala Arg Gly Phe
290                 295                 300

Pro Val Ile Asp Arg Met Lys Ala Ala Val Glu Ser Ala Cys Pro Arg
305                 310                 315                 320

Thr Val Ser Cys Ala Asp Leu Leu Thr Ile Ala Ala Gln Gln Ser Val
                325                 330                 335

Thr Leu Ala Gly Gly Pro Ser Trp Arg Val Pro Leu Gly Arg Arg Asp
            340                 345                 350

Ser Leu Gln Ala Phe Leu Asp Leu Ala Asn Ala Asn Leu Pro Ala Pro
        355                 360                 365
```

-continued

```
Phe Phe Thr Leu Pro Gln Leu Lys Asp Ser Phe Arg Asn Val Gly Leu
    370                 375                 380

Asn Arg Ser Ser Asp Leu Val Ala Leu Ser Gly Gly His Thr Phe Gly
385                 390                 395                 400

Lys Ser Gln Cys Arg Phe Ile Met Asp Arg Leu Tyr Asn Phe Ser Asn
                405                 410                 415

Thr Gly Leu Pro Asp Pro Thr Leu Asn Thr Thr Tyr Leu Gln Thr Leu
            420                 425                 430

Arg Gly Leu Cys Pro Leu Asn Gly Asn Leu Ser Ala Leu Val Asp Phe
        435                 440                 445

Asp Leu Arg Thr Pro Thr Ile Phe Asp Asn Lys Tyr Tyr Val Asn Leu
    450                 455                 460

Glu Glu Gln Lys Gly Leu Ile Gln Ser Asp Gln Glu Leu Phe Ser Ser
465                 470                 475                 480

Pro Asn Ala Thr Asp Thr Ile Pro Leu Val Arg Ser Phe Ala Asn Ser
                485                 490                 495

Thr Gln Thr Phe Phe Asn Ala Phe Val Glu Ala Met Asp Arg Met Gly
            500                 505                 510

Asn Ile Thr Pro Leu Thr Gly Thr Gln Gly Gln Ile Arg Leu Asn Cys
        515                 520                 525

Arg Val Val Asn Ser Asn Ser Asp Leu Lys Asp Glu Leu
    530                 535                 540
```

<210> SEQ ID NO 8
<211> LENGTH: 1623
<212> TYPE: DNA
<213> ORGANISM: Artificial Sequence
<220> FEATURE:
<223> OTHER INFORMATION: nucleotide sequence encoding anti-VEGFA light chain linked to HRP via a (G4S)3 linker

<400> SEQUENCE: 8

```
gcccttgtga tgacccagac tccatcctcc gtgtctgcag ctgtgggaga cacagtcacc     60
atcaagtgcc aggccagtca gagcattaat gcctacttag cctggtatca gcagaaacca    120
gggcagcctc ccaagctcct gatctaccag gcatccaatc tggcatctgg ggtcccatcg    180
cggttcaaag gcagtagatc tgggacagag tacactctca ccatcagcgg cgtgcagcgt    240
gaggatgctg ccacctacta ctgtctaggc actcgtactg ctggtgatgt tgctttcggc    300
ggagggacca aactggaaat caaagatcca gttgcaccta ctgtcctcat cttcccacca    360
gctgctgatc aggtggcaac tggaacagtc accatcgtgt gtgtggcgaa taaatacttt    420
cccgatgtca ccgtcacctg ggaggtggat ggcaccaccc aaacaactgg catcgagaac    480
agtaaaacac cgcagaactc tgcagattgt acctacaacc tcagcagcac tctgacactg    540
accagcacac agtacaacag ccacaaagag tacacctgca aggtgaccca gggcacgacc    600
tcagtcgtcc agagcttcaa caggggtgac tgcggtggag gcggttcagg cggaggtggc    660
tctggcggtg gcggatcgat gcagcttact ccaactttct acgataactc ttgtcctaac    720
gtgagcaaca tcgtgcgaga tactatcgtg aacgagttgc ggtctgatcc gaggatagcc    780
gcttcaattt tgcggctgca tttccacgat tgttttgtaa acggctgtga tgcttccatc    840
ctcctcgaca ataccacctc tttcaggact gaaaaggatg ccttcggtaa cgcgaatagt    900
gctagagggt ttcccgtgat cgatagaatg aaagccgctg tggagagcgc ctgcccccgg    960
acagttagtt gtgcagacct tctgaccata gcggcccagc aatccgtgac gctggccggt   1020
ggccccagct ggagggtccc cctgggaagg agggactctc tgcaggcttt tctggacttg   1080
```

```
gcaaacgcaa acctgcctgc tcccttcttc acccttcccc agctgaagga ttccttcagg    1140
aatgtcggcc tgaaccgaag tagtgatttg gtggctctgt ccggaggcca cacattcggc    1200
aagagtcagt gcaggttcat catggacaga ctgtataact tttccaacac cggcttgcct    1260
gaccctaccc tgaacacaac atacttgcag actctcagag ggctgtgtcc gctcaatggc    1320
aacttgtctg cactggttga ctttgacctg cgcaccccaa ccatcttcga caataagtat    1380
tacgtcaatc tggaggaaca gaagggcctg attcagtccg accaggagct gttcagttcc    1440
ccaaatgcta ccgacactat tcctcttgtg cgcagcttcg ctaatagcac acaaaccttt    1500
ttcaatgctt tcgtggaagc tatggatcgg atgggaaata taacgcccct gacgggtacg    1560
cagggacaga taagactgaa ctgtagggtc gtgaacagca actctgactt gaaggacgaa    1620
ctt                                                                  1623
```

<210> SEQ ID NO 9
<211> LENGTH: 5
<212> TYPE: PRT
<213> ORGANISM: Artificial Sequence
<220> FEATURE:
<223> OTHER INFORMATION: GGGGS linker

<400> SEQUENCE: 9

Gly Gly Gly Gly Ser
1               5

<210> SEQ ID NO 10
<211> LENGTH: 10
<212> TYPE: PRT
<213> ORGANISM: Artificial Sequence
<220> FEATURE:
<223> OTHER INFORMATION: (GGGGS)2 linker

<400> SEQUENCE: 10

Gly Gly Gly Gly Ser Gly Gly Gly Gly Ser
1               5                   10

<210> SEQ ID NO 11
<211> LENGTH: 15
<212> TYPE: PRT
<213> ORGANISM: Artificial Sequence
<220> FEATURE:
<223> OTHER INFORMATION: (GGGGS)3 linker

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 20
<212> TYPE: PRT
<213> ORGANISM: Artificial Sequence
<220> FEATURE:
<223> OTHER INFORMATION: (GGGGS)4 linker

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 25

```
<212> TYPE: PRT
<213> ORGANISM: Artificial Sequence
<220> FEATURE:
<223> OTHER INFORMATION: (GGGGS)5 linker

<400> SEQUENCE: 13

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```